(12) United States Patent
Deransart et al.

(10) Patent No.: US 12,396,862 B2
(45) Date of Patent: Aug. 26, 2025

(54) GLENOID BASEPLATE AND IMPLANT ASSEMBLIES

(71) Applicant: HOWMEDICA OSTEONICS CORP., Mahwah, NJ (US)

(72) Inventors: Pierric Deransart, Saint Martin d'uriage (FR); Pascal Boileau, Bloomington, MN (US); Gilles Walch, Bloomington, MN (US); Charles L. Penninger, Bloomington, MN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 449 days.

(21) Appl. No.: 17/432,228

(22) PCT Filed: May 1, 2020

(86) PCT No.: PCT/US2020/031134
§ 371 (c)(1),
(2) Date: Aug. 19, 2021

(87) PCT Pub. No.: WO2020/231657
PCT Pub. Date: Nov. 19, 2020

(65) Prior Publication Data
US 2022/0183851 A1 Jun. 16, 2022

Related U.S. Application Data

(60) Provisional application No. 62/847,077, filed on May 13, 2019.

(51) Int. Cl.
*A61F 2/40* (2006.01)
*A61F 2/30* (2006.01)

(52) U.S. Cl.
CPC ........ *A61F 2/4081* (2013.01); *A61F 2/30749* (2013.01); *A61F 2002/30433* (2013.01);
(Continued)

(58) Field of Classification Search
CPC ............... A61F 2/4081; A61F 2/30749; A61F 2002/30433; A61F 2002/30797;
(Continued)

(56) References Cited

U.S. PATENT DOCUMENTS 4,550,450 A 11/1985 Kinnett
4,725,280 A 2/1988 Laure
(Continued)

FOREIGN PATENT DOCUMENTS

AU 2012204090 A1 8/2012
DE 10123517 C1 11/2002
(Continued)

OTHER PUBLICATIONS

International Search Report and Written Opinion issued in connection with International Patent Application No. PCT/US2022/034245, Sep. 23, 2022, 16 pages.
(Continued)

*Primary Examiner* — Jerrah Edwards
*Assistant Examiner* — Kia Xiong White
(74) *Attorney, Agent, or Firm* — DUANE MORRIS LLP

(57) ABSTRACT

A glenoid baseplate is provided that has a transverse body and an elongate body. The transverse body has a first side configured to engage scapula bone of a patient, a second side configured to face away from the first side, and a plurality of anchor apertures. The anchor apertures are formed between the first side and the second side. The transverse body also can have an arcuate or circular periphery that has an anterior portion configured to be oriented toward an anterior side of a scapula and a posterior portion that is configured to be oriented toward a posterior side of the scapula. The elongate body is disposed along a longitudinal axis between an end coupled with the first side of the
(Continued)

transverse body. The longitudinal axis of the elongate body is off-set from the center of the circular periphery.

16 Claims, 13 Drawing Sheets

(52) U.S. Cl.
CPC .............. *A61F 2002/30797* (2013.01); *A61F 2002/30813* (2013.01)

(58) Field of Classification Search
CPC .. A61F 2002/30813; A61F 2002/30774; A61F 2002/3079; A61F 2002/30795; A61F 2/40; A61F 2002/4022; A61F 2002/4085; A61F 2002/4629
See application file for complete search history.

(56) References Cited

U.S. PATENT DOCUMENTS

| | | |
|---|---|---|
| 4,986,833 A | 1/1991 | Worland |
| 4,990,161 A | 2/1991 | Kampner |
| 5,032,132 A | 7/1991 | Matsen, III et al. |
| 5,033,036 A | 7/1991 | Ohmori et al. |
| 5,080,673 A | 1/1992 | Burkhead et al. |
| 5,108,446 A | 4/1992 | Wagner et al. |
| 5,458,637 A | 10/1995 | Hayes |
| 5,489,309 A | 2/1996 | Lackey et al. |
| 5,489,311 A | 2/1996 | Cipolletti |
| 5,531,973 A | 7/1996 | Sarv |
| 5,662,657 A | 9/1997 | Carn |
| 5,702,447 A | 12/1997 | Walch et al. |
| 5,800,551 A | 9/1998 | Williamson et al. |
| 5,954,722 A | 9/1999 | Bono |
| 6,102,951 A | 8/2000 | Sutter et al. |
| 6,102,954 A | 8/2000 | Albrektsson et al. |
| 6,139,550 A | 10/2000 | Michelson |
| 6,171,342 B1 | 1/2001 | O'Neil et al. |
| 6,228,119 B1 | 5/2001 | Ondrla et al. |
| 6,228,120 B1 | 5/2001 | Leonard et al. |
| 6,406,495 B1 | 6/2002 | Schoch |
| 6,508,841 B2 | 1/2003 | Martin et al. |
| 6,514,287 B2 | 2/2003 | Ondrla et al. |
| 6,673,115 B2 | 1/2004 | Resch et al. |
| 6,679,916 B1 | 1/2004 | Frankle et al. |
| 6,699,289 B2 | 3/2004 | Iannotti et al. |
| 6,761,740 B2 | 7/2004 | Tornier |
| 6,783,549 B1 | 8/2004 | Stone et al. |
| 6,790,234 B1 | 9/2004 | Frankle |
| 6,860,903 B2 | 3/2005 | Mears et al. |
| 6,911,047 B2 | 6/2005 | Rockwood, Jr. et al. |
| 6,942,699 B2 | 9/2005 | Stone et al. |
| 6,953,478 B2 | 10/2005 | Bouttens et al. |
| 6,969,406 B2 | 11/2005 | Tornier |
| 7,160,328 B2 | 1/2007 | Rockwood, Jr. et al. |
| 7,169,184 B2 | 1/2007 | Pria |
| 7,175,663 B1 | 2/2007 | Stone |
| 7,175,665 B2 | 2/2007 | German et al. |
| 7,204,854 B2 | 4/2007 | Guederian et al. |
| 7,316,715 B2 | 1/2008 | Plaskon |
| 7,431,736 B2 | 10/2008 | Maroney et al. |
| 7,462,197 B2 | 12/2008 | Tornier |
| 7,462,199 B2 | 12/2008 | Justin et al. |
| 7,527,631 B2 | 5/2009 | Maroney et al. |
| 7,604,665 B2 | 10/2009 | Iannotti et al. |
| 7,608,109 B2 | 10/2009 | Dalla Pria |
| 7,611,539 B2 | 11/2009 | Bouttens et al. |
| 7,621,961 B2 | 11/2009 | Stone |
| 7,637,928 B2 | 12/2009 | Fernandez |
| 7,648,530 B2 | 1/2010 | Habermeyer et al. |
| 7,666,522 B2 | 2/2010 | Justin et al. |
| 7,753,959 B2 | 7/2010 | Berelsman et al. |
| 7,766,969 B2 | 8/2010 | Justin et al. |
| 7,854,768 B2 | 12/2010 | Wiley et al. |
| 7,883,653 B2 | 2/2011 | Smith et al. |
| 7,892,287 B2 | 2/2011 | Deffenbaugh |
| 7,922,769 B2 | 4/2011 | Deffenbaugh et al. |
| 7,927,335 B2 | 4/2011 | Deffenbaugh et al. |
| 7,993,408 B2 | 8/2011 | Meridew et al. |
| 8,007,523 B2 | 8/2011 | Wagner et al. |
| 8,048,161 B2 | 11/2011 | Guederian et al. |
| 8,062,376 B2 | 11/2011 | Shultz et al. |
| 8,070,820 B2 | 12/2011 | Winslow et al. |
| 8,092,545 B2 | 1/2012 | Coon et al. |
| 8,206,453 B2 | 6/2012 | Cooney, III et al. |
| 8,231,683 B2 | 7/2012 | Lappin et al. |
| 8,241,365 B2 | 8/2012 | Williams, Jr. et al. |
| 8,287,600 B2 | 10/2012 | Angibaud |
| 8,308,807 B2 | 11/2012 | Seebeck et al. |
| 8,357,201 B2 | 1/2013 | Mayer et al. |
| 8,361,157 B2 | 1/2013 | Bouttens et al. |
| 8,425,614 B2 | 4/2013 | Winslow et al. |
| 8,444,680 B2 | 5/2013 | Dooney, Jr. et al. |
| 8,449,617 B1 | 5/2013 | McDaniel et al. |
| 8,454,702 B2 | 6/2013 | Smits et al. |
| 8,454,705 B2 | 6/2013 | Pressacco et al. |
| 8,465,548 B2 | 6/2013 | Long |
| 8,480,750 B2 | 7/2013 | Long |
| 8,532,806 B1 | 9/2013 | Masson |
| 8,556,901 B2 | 10/2013 | Anthony et al. |
| 8,556,902 B2 | 10/2013 | Ek et al. |
| 8,556,980 B2 | 10/2013 | Deffenbaugh |
| 8,556,981 B2 | 10/2013 | Jones et al. |
| 8,591,591 B2 | 11/2013 | Winslow et al. |
| 8,597,334 B2 | 12/2013 | Mocanu |
| 8,632,597 B2 | 1/2014 | Lappin |
| 8,690,951 B2 | 4/2014 | Baum et al. |
| 8,690,952 B2 | 4/2014 | Dallmann |
| 8,753,402 B2 | 6/2014 | Winslow et al. |
| 8,790,402 B2 | 7/2014 | Monaghan et al. |
| 8,840,676 B2 | 9/2014 | Belew |
| 8,864,834 B2 | 10/2014 | Boileau et al. |
| 8,870,886 B2 | 10/2014 | Burgi |
| 8,961,611 B2 | 2/2015 | Long |
| 9,114,017 B2 | 8/2015 | Lappin |
| 9,233,003 B2 | 1/2016 | Roche et al. |
| 9,498,345 B2 | 11/2016 | Burkhead et al. |
| 9,512,445 B2 | 12/2016 | Iannotti |
| 9,629,725 B2 | 4/2017 | Gargac et al. |
| 9,763,682 B2 | 9/2017 | Bettenga |
| 9,782,208 B2 | 10/2017 | Martin |
| 9,839,436 B2 | 12/2017 | Kehres et al. |
| 10,034,757 B2 | 7/2018 | Kovacs et al. |
| 10,064,734 B2 | 9/2018 | Burkhead et al. |
| 10,251,755 B2 | 4/2019 | Boileau et al. |
| 10,342,669 B2 | 7/2019 | Hopkins |
| 10,357,373 B2 | 7/2019 | Gargac et al. |
| 10,463,499 B2 | 11/2019 | Emerick et al. |
| 10,583,012 B1 | 3/2020 | Longobardi |
| 10,722,374 B2 | 7/2020 | Hodorek et al. |
| 10,779,952 B2 | 9/2020 | Gunther et al. |
| 10,945,862 B2 | 3/2021 | Roby et al. |
| 2001/0011192 A1 | 8/2001 | Ondrla et al. |
| 2001/0037153 A1 | 11/2001 | Rockwood et al. |
| 2002/0095214 A1 | 7/2002 | Hyde, Jr. |
| 2003/0055507 A1 | 3/2003 | McDevitt et al. |
| 2003/0149485 A1 | 8/2003 | Tornier |
| 2004/0030394 A1 | 2/2004 | Horber |
| 2004/0059424 A1 | 3/2004 | Guederian et al. |
| 2004/0106928 A1 | 6/2004 | Ek |
| 2004/0220673 A1 | 11/2004 | Pria |
| 2004/0220674 A1 | 11/2004 | Pria |
| 2005/0049709 A1 | 3/2005 | Tornier |
| 2005/0060039 A1 | 3/2005 | Cyprien |
| 2005/0085915 A1 | 4/2005 | Steinberg |
| 2005/0143831 A1 | 6/2005 | Justin et al. |
| 2005/0149044 A1 | 7/2005 | Justin et al. |
| 2005/0192673 A1 | 9/2005 | Saltzman et al. |
| 2005/0256583 A1 | 11/2005 | Bouttens et al. |
| 2005/0261775 A1 | 11/2005 | Baum et al. |
| 2005/0278030 A1 | 12/2005 | Tornier |
| 2006/0069443 A1 | 3/2006 | Deffenbaugh et al. |
| 2006/0069444 A1 | 3/2006 | Deffenbaugh |

(56) References Cited

U.S. PATENT DOCUMENTS

| | | |
|---|---|---|
| 2006/0074353 A1 | 4/2006 | Deffenbaugh et al. |
| 2006/0074430 A1 | 4/2006 | Deffenbaugh et al. |
| 2006/0100714 A1 | 5/2006 | Ensign |
| 2006/0111787 A1 | 5/2006 | Bailie et al. |
| 2006/0122705 A1 | 6/2006 | Morgan |
| 2006/0142865 A1 | 6/2006 | Hyde |
| 2006/0200248 A1 | 9/2006 | Beguin et al. |
| 2006/0200249 A1 | 9/2006 | Beguin et al. |
| 2007/0016304 A1 | 1/2007 | Chudik |
| 2007/0055380 A1 | 3/2007 | Berelsman et al. |
| 2007/0100458 A1 | 5/2007 | Dalla Pria |
| 2007/0142921 A1 | 6/2007 | Lewis et al. |
| 2007/0156246 A1 | 7/2007 | Meswania et al. |
| 2007/0179624 A1 | 8/2007 | Stone et al. |
| 2007/0219638 A1 | 9/2007 | Jones et al. |
| 2007/0244563 A1 | 10/2007 | Roche et al. |
| 2007/0244564 A1 | 10/2007 | Ferrand et al. |
| 2007/0260321 A1 | 11/2007 | Stchur |
| 2008/0140130 A1 | 6/2008 | Chan et al. |
| 2008/0183297 A1 | 7/2008 | Boileau et al. |
| 2008/0255568 A1 | 10/2008 | Tornier et al. |
| 2008/0269906 A1 | 10/2008 | Iannotti et al. |
| 2008/0294268 A1 | 11/2008 | Baum et al. |
| 2008/0306601 A1 | 12/2008 | Dreyfuss |
| 2009/0125113 A1 | 5/2009 | Guederian et al. |
| 2009/0149961 A1 | 6/2009 | Dallmann |
| 2009/0164021 A1 | 6/2009 | Dallmann |
| 2009/0204225 A1 | 8/2009 | Meridew et al. |
| 2009/0216332 A1 | 8/2009 | Splieth et al. |
| 2009/0281630 A1 | 11/2009 | Delince et al. |
| 2009/0281632 A1 | 11/2009 | Naidu |
| 2009/0292364 A1 | 11/2009 | Linares |
| 2010/0016975 A1 | 1/2010 | Iannotti et al. |
| 2010/0023068 A1 | 1/2010 | Bouttens et al. |
| 2010/0049327 A1 | 2/2010 | Isch et al. |
| 2010/0087927 A1 | 4/2010 | Roche et al. |
| 2010/0161066 A1 | 6/2010 | Iannotti et al. |
| 2010/0217399 A1 | 8/2010 | Groh |
| 2010/0234959 A1 | 9/2010 | Roche et al. |
| 2010/0249938 A1 | 9/2010 | Gunther et al. |
| 2010/0274359 A1 | 10/2010 | Brunnarius et al. |
| 2010/0291401 A1 | 11/2010 | Medina et al. |
| 2010/0331990 A1 | 12/2010 | Mroczkowski |
| 2011/0029089 A1 | 2/2011 | Giuliani et al. |
| 2011/0035013 A1 | 2/2011 | Winslow et al. |
| 2011/0106266 A1 | 5/2011 | Schwyzer et al. |
| 2011/0118846 A1 | 5/2011 | Katrana et al. |
| 2011/0144758 A1 | 6/2011 | Deffenbaugh |
| 2011/0144760 A1 | 6/2011 | Wong et al. |
| 2011/0152869 A1 | 6/2011 | Ek et al. |
| 2011/0190899 A1 | 8/2011 | Pierce et al. |
| 2011/0224673 A1 | 9/2011 | Smith |
| 2011/0282393 A1 | 11/2011 | Garlach et al. |
| 2012/0004733 A1 | 1/2012 | Hodorek et al. |
| 2012/0029647 A1 | 2/2012 | Winslow et al. |
| 2012/0059383 A1 | 3/2012 | Murphy et al. |
| 2012/0078258 A1 | 3/2012 | Lo et al. |
| 2012/0109320 A1 | 5/2012 | Walch et al. |
| 2012/0123419 A1 | 5/2012 | Purdy et al. |
| 2012/0130498 A1 | 5/2012 | Long |
| 2012/0165954 A1 | 6/2012 | Nimal |
| 2012/0191201 A1 | 7/2012 | Smits et al. |
| 2012/0209392 A1 | 8/2012 | Angibaud et al. |
| 2012/0221112 A1 | 8/2012 | Lappin |
| 2012/0232670 A1 | 9/2012 | Bojarski et al. |
| 2012/0239051 A1 | 9/2012 | de Wilde et al. |
| 2012/0239156 A1 | 9/2012 | De Wilde et al. |
| 2012/0253467 A1* | 10/2012 | Frankle ................ A61F 2/4014 623/19.11 |
| 2012/0277880 A1 | 11/2012 | Winslow et al. |
| 2013/0018483 A1 | 1/2013 | Li et al. |
| 2013/0053968 A1 | 2/2013 | Nardini et al. |
| 2013/0066433 A1 | 3/2013 | Veronesi et al. |
| 2013/0096631 A1 | 4/2013 | Leung et al. |
| 2013/0110116 A1 | 5/2013 | Kehres et al. |
| 2013/0110470 A1 | 5/2013 | Vanasse et al. |
| 2013/0144393 A1 | 6/2013 | Mutchler et al. |
| 2013/0150972 A1 | 6/2013 | Iannotti et al. |
| 2013/0150973 A1 | 6/2013 | Splieth et al. |
| 2013/0150975 A1 | 6/2013 | Iannotti et al. |
| 2013/0226186 A1 | 8/2013 | Burgi |
| 2013/0226309 A1 | 8/2013 | Daigo et al. |
| 2013/0231754 A1 | 9/2013 | Daigo et al. |
| 2013/0253656 A1 | 9/2013 | Long |
| 2013/0261751 A1 | 10/2013 | Lappin |
| 2013/0261752 A1 | 10/2013 | Lappin et al. |
| 2013/0264749 A1 | 10/2013 | Jones et al. |
| 2013/0282135 A1 | 10/2013 | Sun et al. |
| 2013/0338675 A1 | 12/2013 | Nelson et al. |
| 2014/0005789 A1 | 1/2014 | Chavarria et al. |
| 2014/0012266 A1 | 1/2014 | Bonin, Jr. et al. |
| 2014/0018927 A1 | 1/2014 | de Wilde et al. |
| 2014/0025173 A1 | 1/2014 | Cardon et al. |
| 2014/0142711 A1 | 5/2014 | Maroney et al. |
| 2014/0163564 A1 | 6/2014 | Bollinger |
| 2014/0194995 A1 | 7/2014 | Koka |
| 2014/0243986 A1 | 8/2014 | Frankle |
| 2014/0257499 A1 | 9/2014 | Winslow et al. |
| 2014/0277180 A1 | 9/2014 | Paolino et al. |
| 2014/0277517 A1 | 9/2014 | Winslow |
| 2014/0277518 A1 | 9/2014 | Iannotti |
| 2014/0277520 A1 | 9/2014 | Chavarria et al. |
| 2014/0316416 A1 | 10/2014 | Liu et al. |
| 2014/0371863 A1 | 12/2014 | Vanasse et al. |
| 2015/0073424 A1 | 3/2015 | Couture et al. |
| 2015/0094819 A1 | 4/2015 | Iannotti et al. |
| 2015/0142122 A1 | 5/2015 | Bickley et al. |
| 2015/0150688 A1 | 6/2015 | Vanasse et al. |
| 2015/0265292 A1 | 9/2015 | Olson |
| 2015/0272741 A1 | 10/2015 | Taylor et al. |
| 2016/0045323 A1 | 2/2016 | Kovacs et al. |
| 2016/0151164 A1 | 6/2016 | Taylor et al. |
| 2016/0166392 A1 | 6/2016 | Vanasse et al. |
| 2016/0199074 A1 | 7/2016 | Winslow et al. |
| 2016/0206436 A1 | 7/2016 | Chavarria et al. |
| 2016/0228262 A1 | 8/2016 | Bailey |
| 2016/0256222 A1 | 9/2016 | Walch |
| 2016/0270922 A1 | 9/2016 | Pressacco et al. |
| 2016/0287266 A1 | 10/2016 | Sikora et al. |
| 2016/0287401 A1 | 10/2016 | Muir et al. |
| 2016/0310285 A1 | 10/2016 | Kovacs et al. |
| 2016/0324649 A1 | 11/2016 | Hodorek et al. |
| 2016/0354209 A1 | 12/2016 | Van Kampen et al. |
| 2016/0367375 A1 | 12/2016 | Boulris |
| 2017/0027709 A1 | 2/2017 | Winslow et al. |
| 2017/0042687 A1 | 2/2017 | Boileau et al. |
| 2017/0042690 A1 | 2/2017 | Burkhead et al. |
| 2017/0049574 A1 | 2/2017 | Hopkins |
| 2017/0172764 A1 | 6/2017 | Muir et al. |
| 2017/0273795 A1 | 9/2017 | Neichel et al. |
| 2017/0273801 A1 | 9/2017 | Hodorek et al. |
| 2017/0273806 A1 | 9/2017 | Cardon et al. |
| 2017/0367836 A1 | 12/2017 | Cardon et al. |
| 2018/0014941 A1 | 1/2018 | Frankle et al. |
| 2018/0064537 A1 | 3/2018 | Pressacco et al. |
| 2018/0078377 A1 | 3/2018 | Gargac et al. |
| 2018/0085226 A1 | 3/2018 | Baumgarten |
| 2018/0092747 A1 | 4/2018 | Hopkins |
| 2018/0161169 A1 | 6/2018 | Cardon et al. |
| 2018/0243102 A1 | 8/2018 | Burkhead, Jr. et al. |
| 2018/0303618 A1 | 10/2018 | Kovacs et al. |
| 2018/0368982 A1 | 12/2018 | Ball |
| 2019/0015116 A1 | 1/2019 | Gargac et al. |
| 2019/0015117 A1 | 1/2019 | Neichel et al. |
| 2019/0015221 A1* | 1/2019 | Neichel ................ A61F 2/4081 |
| 2019/0029833 A1 | 1/2019 | Briscoe et al. |
| 2019/0076261 A1 | 3/2019 | Mutchler et al. |
| 2019/0336293 A1 | 11/2019 | Kehres |
| 2020/0030108 A1 | 1/2020 | Orphanos et al. |
| 2020/0179126 A1 | 6/2020 | Courtney, Jr. et al. |
| 2020/0188121 A1 | 6/2020 | Boux De Casson et al. |
| 2020/0188125 A1 | 6/2020 | Hodorek et al. |
| 2020/0237519 A1* | 7/2020 | Ball ................ A61F 2/4612 |
| 2020/0289180 A1 | 9/2020 | Martin et al. |

(56) References Cited

U.S. PATENT DOCUMENTS

| | | |
|---|---|---|
| 2020/0289282 A1 | 9/2020 | Lefebvre et al. |
| 2020/0368031 A1 | 11/2020 | Hodorek et al. |
| 2020/0405491 A1 | 12/2020 | Cleveland et al. |
| 2021/0030552 A1 | 2/2021 | Terrill |
| 2021/0030553 A1 | 2/2021 | Terrill |
| 2021/0045895 A1 | 2/2021 | Sapio et al. |
| 2021/0298910 A1 | 9/2021 | Gargac et al. |
| 2021/0307911 A1 | 10/2021 | Metcalfe et al. |
| 2021/0338456 A1 | 11/2021 | Wolfe et al. |
| 2021/0369465 A1 | 12/2021 | Simoes et al. |
| 2022/0151793 A1 | 5/2022 | Deransart et al. |
| 2022/0151794 A1 | 5/2022 | Fattori et al. |
| 2022/0175543 A1 | 6/2022 | Ball |
| 2022/0202580 A1 | 6/2022 | Wilkins et al. |
| 2022/0241077 A1 | 8/2022 | Hodorek et al. |
| 2022/0280306 A1 | 9/2022 | Metcalfe et al. |
| 2022/0296381 A1 | 9/2022 | Ek et al. |
| 2022/0313440 A1 | 10/2022 | Metcalfe et al. |
| 2022/0395376 A1 | 12/2022 | Poon et al. |
| 2023/0000636 A1 | 1/2023 | Dalla Pria et al. |
| 2023/0114073 A1 | 4/2023 | Perego |
| 2023/0285154 A1 | 9/2023 | Picha et al. |

FOREIGN PATENT DOCUMENTS

| | | |
|---|---|---|
| EP | 0581667 | 2/1994 |
| EP | 0776636 | 6/1997 |
| EP | 1013246 | 11/1999 |
| EP | 1064890 | 1/2001 |
| EP | 1323395 | 7/2003 |
| EP | 1488764 B1 | 12/2006 |
| EP | 1762201 A1 | 3/2007 |
| EP | 1639949 B1 | 8/2007 |
| EP | 1639967 B1 | 7/2008 |
| EP | 1515758 B1 | 3/2009 |
| EP | 2057970 | 5/2009 |
| EP | 1776935 B1 | 8/2009 |
| EP | 1639966 B1 | 9/2009 |
| EP | 2201912 A1 | 6/2010 |
| EP | 1927328 B1 | 1/2011 |
| EP | 1902689 B1 | 11/2011 |
| EP | 2564814 A1 | 3/2013 |
| EP | 1996125 B1 | 5/2013 |
| EP | 2335655 B1 | 7/2013 |
| EP | 1951161 B1 | 4/2014 |
| EP | 1973498 B1 | 4/2014 |
| EP | 2481376 B1 | 4/2014 |
| EP | 2601912 B1 | 7/2016 |
| EP | 3291768 B1 | 11/2019 |
| EP | 3412252 B1 | 2/2020 |
| EP | 3679900 A1 | 7/2020 |
| EP | 3756625 A1 | 12/2020 |
| FR | 2567019 | 1/1986 |
| FR | 2739151 A1 | 3/1997 |
| FR | 2776506 B1 | 8/2000 |
| FR | 2790662 B1 | 6/2001 |
| FR | 2825263 A1 | 12/2002 |
| FR | 2821545 B1 | 8/2003 |
| FR | 2955248 B1 | 3/2012 |
| FR | 2971144 A1 | 8/2012 |
| FR | 2977791 B1 | 7/2014 |
| GB | 2297257 A | 7/1996 |
| WO | 2001054561 A2 | 8/2001 |
| WO | 2011044879 A1 | 4/2011 |
| WO | WO 2011/073169 | 6/2011 |
| WO | WO 2011/150180 A2 | 12/2011 |
| WO | 2013064569 A1 | 5/2013 |
| WO | 2015051476 A1 | 4/2015 |
| WO | WO 2015/068035 | 5/2015 |
| WO | WO 2015/103090 | 7/2015 |
| WO | 2015130006 A1 | 9/2015 |
| WO | 2016025712 A2 | 2/2016 |
| WO | WO 2017/007565 | 1/2017 |
| WO | 2019014278 A1 | 1/2019 |
| WO | 2019079104 A2 | 4/2019 |
| WO | WO 2019/079104 | 4/2019 |
| WO | 2020033911 A1 | 2/2020 |
| WO | 2020154611 A1 | 7/2020 |
| WO | 2020219962 A1 | 10/2020 |
| WO | WO 2020/231657 | 11/2020 |
| WO | 2021030146 A1 | 2/2021 |
| WO | 2021178418 A1 | 9/2021 |
| WO | 2021216405 A3 | 12/2021 |
| WO | 2022147376 A1 | 7/2022 |
| WO | 2022261508 A1 | 12/2022 |

OTHER PUBLICATIONS

International Search Report and Written Opinion issued in connection with International Patent Application No. PCT/US2023/070118, Mar. 1, 2024, 15 pages.

International Search Report and Written Opinion issued in connection with International Patent Application No. PCT/US2022/080550, Apr. 10, 2023, 16 pages.

International Search Report and Written Opinion issued in connection with International Patent Application No. PCT/US2022/035217, Nov. 1, 2022, 14 pages.

International Search Report and Written Opinion issued in connection with International Patent Application No. PCT/US2023/064983, Sep. 29, 2023, 10 pages.

EP Search Report and Written Opinion issued in European Patent Application No. 12153346.7, dated Mar. 8, 2012, in 6 pages.

French Search Report and Written Opinion issued in Application. No. FR1150994, mailed May 27, 2011, in 7 pages.

Anatomical Shoulder™ Inverse/Reverse System Surgical Technique, Product Brochure, Zimmer, Inc., published 2006, in 32 pages.

Arthrex, "Arthrex Releases Univers Revers™ Shoulder Arthroplasty System in the United States—First Surgery Successfully Performed in Chillicothe, OH", Jun. 18, 2013.

Biomet, "Comprehensive® Reverse Shoulder System", 2013.

Boileau et al., "Cemented polyethylene versus uncemented metal-backed glenoid components in total shoulder arthroplasty: A prospective, double-blind, randomized study," Journal of Shoulder and Elbow Surgery, Jul./Aug. 2002, vol. 11, Issue 4, pp. 351-359.

Boileau et al., "Metal-backed glenoid implant with polyethylene insert is not a viable long-term therapeutic option," Journal of Shoulder and Elbow Surgery, Feb. 2015, pp. 1-10.

Cementless Fixation Using a Polyethyene Oseo-Integration Peg as Used on the Freeman-Samuelson Knee brochure, produced by Finsbury Instruments Limited London in conjunction with Adrian Tuke Limited, 1982.

Castagna et al., "Mid-term results of a metal-backed glenoid component in total shoulder replacement," The Journal of Bone and Joint Surgery, Oct. 2010, vol. 92-B, No. 10, pp. 1410-1415.

Clement et al., "An uncemented metal-backed glenoid component in total shoulder arthroplasty for osteoarthritis: factors affecting survival and outcome," The Japanese Orthopaedic Association, published online Sep. 26, 2012, vol. 18, pp. 22-28.

DJO Surgical, Reverse® shoulder prosthesis Surgical Technique, Feb. 2008.

Eclipse™ Stemless Shoulder Prosthesis, Surgical Technique Guide, Anthrex GmbH, 2014, in 12 pages.

Epoca Shoulder Arthroplasty System, Synthes, Inc., Apr. 2008, in 4 pages.

Epoca Shoulder Arthroplasty System—Stem and Glenoid Technique Guide, Synthes, Inc., Apr. 2008, in 56 pages.

Innovative Design Orthopaedics, "Verso® Shoulder Surgical Technique", 2013.

Kany et al., "A convertible shoulder system: is it useful in total shoulder arthroplasty revisions?" International Orthopaedics, published online Oct. 16, 2014, vol. 39, pp. 299-304.

Katz et al., "New design of a cementless glenoid component in unconstrained shoulder arthroplasty: a prospective medium-term analysis of 143 cases," published online Oct. 27, 2012, vol. 23, pp. 27-34.

(56) References Cited

OTHER PUBLICATIONS

Montoya et al., "Midterm results of a total shoulder prosthesis fixed with a cementless glenoid component," Journal of Shoulder and Elbow Surgery, May 2013, vol. 22, Issue 5, pp. 628-635.
SMR Axioma® TT Metal Back Surgical Technique, Product Brochure, Lima Corporate, dated Sep. 2013, in 48 pages.
Taunton et al., "Total Shoulder Arthroplasty with a Metal-Backed, Bone-Ingrowth Glenoid Component," The Journal of Bone and Joint Surgery, Oct. 2008, vol. 90-A, Issue 10, pp. 2180-2188.
Teissier et al., "The TESS reverse shoulder arthroplasty without a stem in the treatment of cuff-deficient shoulder conditions: clinical and radiographic results," Journal of Shoulder and Elbow Surgery, Jan. 2015, vol. 24, Issue 1, pp. 45-51.
The Anatomical Shoulder™: A true system approach, Product Brochure, Zimmer UK Ltd, printed 2006, in 6 pages.
Univers Revers™ Total Shoulder System, Surgical Technique Guide, Anthrex Inc., Version D, revised Jul. 2, 2015, in 28 pages.
International Search Report and Written Opinion for PCT International Application No. PCT/US2020/031134 issued Sep. 30, 2020.
Notice of Allowance issued in connection with U.S. Appl. No. 17/172,789, filed Jul. 20, 2023, 8 pages.
Extended European Search Report issued in connection with European Patent Application No. 22201630.5, Feb. 9, 2023, 8 pages.
Non-Final Office Action issued in connection with U.S. Appl. No. 17/149,308, filed May 23, 2023, 12 pages.
Non-Final Office Action issued in connection with U.S. Appl. No. 16/756,429, filed May 6, 2022, 24 pages.
International Search Report and Written Opinion issued in connection with International Patent Application No. PCT/US2022/011217, May 4, 2022, 15 pages.
International Search Report and Written Opinion issued in connection with International Patent Application No. PCT/US2022/06106, May 11, 2022, 12 pages.
Second Office Action issued in connection with Japanese Patent Application No. 2022-507908, Jun. 20, 2023, 7 pages.
First Office Action issued in connection with Japanese Patent Application No. 2023-532755, Jul. 9, 2024, 4 pages.
Examination Report issued in connection with Australian Patent Application No. 202143348, Jun. 28, 2024, 6 pages.
Non-Final Office Action issued in connection with U.S. Appl. No. 17/597,486, filed Jul. 16, 2024, 8 pages.
First Examination Report issued in connection with Australian Patent Application No. 2022227496, May 16, 2024, 5 pages.
Extended European Search Report issued in connection with European Patent Application No. 21916574.3, Jul. 4, 2024, 8 pages.
Extended European Search Report issued in connection with European Patent Application No. 22753403.9, Jul. 4, 2024, 8 pages.
Extended European Search Report issued in connection with European Patent Application No. 24191670.9, Feb. 20, 2025, 13 pages.
Communication Under Rule 164(2)(b) issued in connection with European Patent Application No. 20758408.7, Feb. 28, 2025, 9 pages.
International Search Report and Written Opinion issued in connection with International Patent Application No. PCT/US2024/050431, Feb. 11, 2025, 7 pages.
Extended European Search Report issued in connection with European Patent Application No. 22760169.7, Oct. 29, 2024, 9 pages.
Partial European Search Report issued in connection with European Patent Application No. 24191670.9, Oct. 18, 2024, 11 pages.
Second Examination Report issued in connection with Australian Patent Application No. 2022227496, Aug. 29, 2024, 7 pages.
Extended European Search Report issued in connection with European Patent Application No. 22846386.5, Mar. 12, 2025, 7 pages.
Extended European Search Report issued in connection with European Patent Application No. 22856384.7, Mar. 18, 2025, 5 pages.
Extended European Search Report issued in connection with European Patent Application No. 24219566.7, Mar. 27, 2025, 8 pages.
International Search Report and Written Opinion issued in connection with International Patent Application No. PCT/US2025/016710, Apr. 8, 2025, 11 pages.

* cited by examiner

GLENOID BASEPLATE AND IMPLANT ASSEMBLIES

INCORPORATION BY REFERENCE TO ANY PRIORITY APPLICATIONS

This application is a National Stage Application, filed under 35 U.S.C. 371, of International Patent Application No. PCT/US2020/031134, filed on May 1, 2020, which claims priority to U.S. Provisional Patent Application No. 62/847,077 filed May 13, 2019, the entireties of which are incorporated herein by reference.

BACKGROUND OF THE INVENTION

Field of the Invention

This application is directed to improved glenoid baseplate designs that are capable of being coupled to a scapula at a glenoid surface and that can have an anchor peg disposed medial of the glenoid surface and between anterior and posterior faces of the scapula.

Description of the Related Art

Shoulder joint conditions can sometimes be resolved with shoulder arthroplasty. More and more, efforts are being focused on making total shoulder joint arthroplasty available to patients who would benefit from such treatment. In a total shoulder joint arthroplasty, the glenoid is typically reamed and a glenoid articular component is mounted to scapula following reaming. The articular component provides a smooth surface for movement of a humeral head or humeral articular component.

A glenoid baseplate can be used to support the glenoid articular component on the scapula. The glenoid baseplate can include an anchor peg on the medial side thereof that is configured to be inserted into scapular bone as part of securing the glenoid baseplate to the scapula.

SUMMARY OF THE INVENTION

While glenoid baseplates are known, one challenge faced in implanting such baseplates is assuring that the anchor peg (or other medial projection) of the baseplate is consistently embedded in, e.g., fully enclosed within, the scapula bone and does not extend through a posterior or anterior wall of the scapula.

In some examples, methods are used to produce a glenoid baseplate that can include a elongate body, e.g., an anchor peg, that can be positioned on a transverse body of the baseplate in a position to extend into a deep part or even a deepest part of the scapula beneath the glenoid surface. The anchor peg position can be matched to the geometry beneath the glenoid (sometimes referred to as vault geometer) to provide a long or even a longest anchor peg that would fit in the portion of the vault selected for the anchor. In some cases the position is chosen such that the anchor peg does not perforate a wall of the scapula.

In one embodiment, a glenoid baseplate is provided that has a transverse body and an elongate body. The transverse body has a first side configured to engage scapula bone of a patient, a second side configured to face away from the first side, and a plurality of anchor apertures. The anchor apertures are formed between the first side and the second side. The transverse body also can have a circular periphery that extends between the first side and the second side. The circular periphery has an anterior portion configured to be oriented toward an anterior side of a scapula and a posterior portion that is configured to be oriented toward a posterior side of the scapula. The circular periphery can have a center. The elongate body is disposed along a longitudinal axis between a first end and a second end. The second end is coupled with the first side of the transverse body. The first end is disposed away from the second end. The longitudinal axis of the elongate body is off-set from the center of the circular periphery toward the anterior portion thereof.

Anchor apertures through the baseplate can be fixed relative to the baseplate such that a surgeon can advance a bone anchor through each anchor aperture without determining an angle or orientation of the anchor member during the time of surgery, eliminating a step of determining the angle or orientation.

Anchor apertures can be configured to enable the surgeon to select the angle of an anchor member relative to the baseplate or through the anchor aperture at the time of the surgery. Segmented threads can allow the angle of the anchor member through the anchor aperture to be selected at the time of surgery. Angling an internal member that is configured to tilt, rotate or swivel can allow for the selection of an orientation of the anchor member relative to the baseplate at the time of surgery.

In another embodiment, a glenoid baseplate is provided that includes a transverse plate and an anchor peg. The transverse plate has a medial side configured to engage scapula bone of a patient, a lateral side configured to face away from the medial side, a plurality of bone screw holes formed between the medial side and the lateral side, and a circular periphery. The circular periphery extends between the medial side and the lateral side. The circular periphery has an anterior portion configured to be oriented toward an anterior side of a scapula, a posterior portion configured to be oriented toward a posterior side of the scapula, and a center. The anchor peg is disposed along a longitudinal axis between a lateral end coupled with the medial side of the transverse plate and a medial end disposed away from the lateral end. The longitudinal axis of the anchor peg is off-set from the center of the circular periphery toward the anterior portion thereof.

In another embodiment, a method is performed or instructed in which a glenoid anchor is provided. The glenoid anchor has a transverse member and a projection. The transverse member has a medial side, a lateral side, an anterior periphery, and a posterior periphery. The projection extends from the medial side. The projection is located closer to the anterior periphery than to the posterior periphery. In the method, a blind hole is formed in a lateral portion of the scapula. The blind hole is formed along a trajectory that is off set from a center of an inferior portion of a glenoid. The blind hole has an opening at the glenoid and an enclosed end opposite the opening. The enclosed end is spaced apart from an anterior surface of the scapula. The enclosed end is spaced apart from a posterior surface of the scapula. The projection of the glenoid anchor is advanced into the blind hole such that the projection is enclosed within the scapula along the blind hole between the opening and the enclosed end.

In another embodiment, a method is performed in which image data responsive to a scan of a scapula of a patient is received. An anchor trajectory extending medially from a lateral surface of the scapula is identified from the image data. The anchor trajectory is at a selected position relative to, e.g., spaced apart from, an anterior surface of the scapula. The anchor trajectory can be at a selected position relative to, e.g., spaced apart from, a posterior surface of the scapula. The spacing of at least one of the anchor trajectory from the anterior surface or the anchor trajectory from the posterior surface is based on the imaging information. A glenoid anchor that has a transverse member and a projection is formed. The glenoid anchor has a medial side, a periphery bounding the medial side, a lateral side, an anterior portion, and a posterior portion. The projection extends from the medial side. The projection is disposed within the periphery at a location aligned with the identified anchor trajectory when the periphery is aligned with the curvature of the inferior portion of the glenoid rim.

In some cases, the periphery bounding the medial side corresponds to a curvature of portion of a glenoid rim of the patient. For instance, the periphery can correspond to an inferior portion of the glenoid rim of the patient. The periphery can correspond to a curvature of another portion of the glenoid if the inferior portion of the glenoid rim is subject to deformity. The periphery can be independent of the shape or curvature of the rim of the patient in some cases.

In some examples an approach is used in which some perforation of a wall of the scapula beneath the glenoid surface is desired, e.g., to provide for bi-cortical fixation of an anchor peg or other elongate member. This approach can be combined with an approach to select a location for the anchor peg or other elongate anchor member that extends into a relatively deep portion of the area under the glenoid (e.g., the vault).

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION OF THE PREFERRED EMBODIMENT

Figure 1:
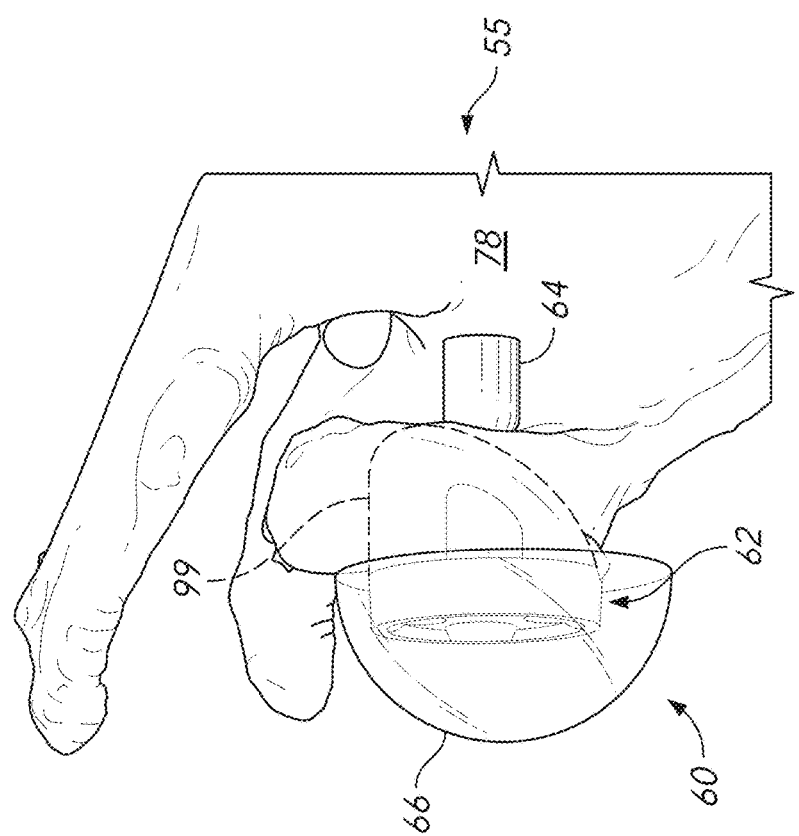
FIG. 1 shows a model of a human humerus and a scapula with a glenoid, the glenoid having an articular assembly coupled thereto, the articular assembly including a glenoid baseplate with a medial end that projects through a posterior wall of the scapula, the humerus having a reverse implant assembly coupled thereto.
Figure 1:
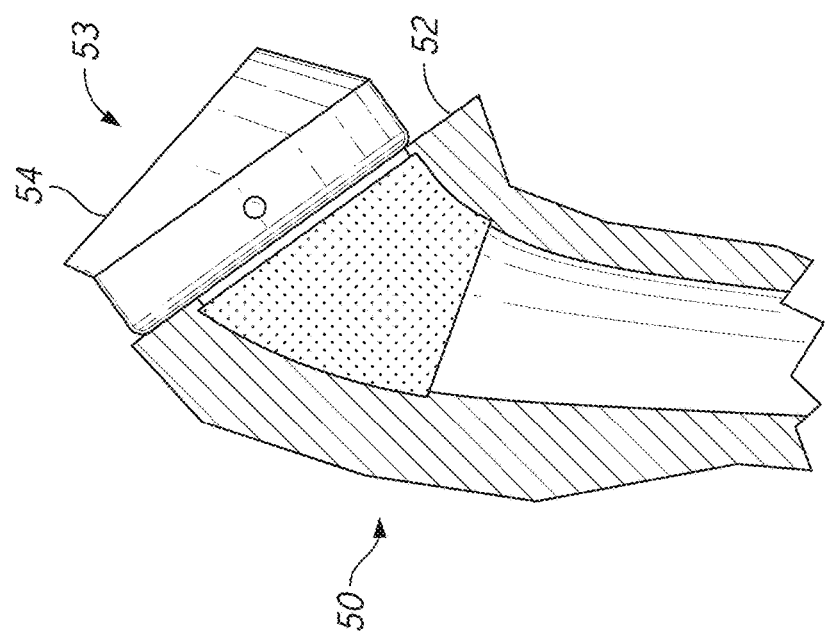

This application is directed to improving the success in providing sound connection between a glenoid assembly and a human scapula. These improvements are intended to allow for greater success in shoulder arthroplasty surgery. FIGS. 1 and 2 illustrate concerns that can arise in some shoulder procedure. FIG. 1 shows a schematic view of a humerus 50 and a scapula 55 of a shoulder having reverse shoulder implants disposed therein. The humerus 50 has a humeral resection 52. A humeral implant assembly 53 including a humeral anchor (shown beneath the humeral resection 52) and a reverse articular body 54. The reverse articular body 54 can be disposed above the humeral resection 52 or at least partially below the humeral resection 52 in some cases. The scapula 55 has a lateral surface 56 that includes a glenoid 58 (see FIG. 1A). The glenoid 58 is the portion of the scapula 55 on which the head of the humerus 50 normally articulates. Following total shoulder arthroplasty, this function is provided by an articular body 66 that is coupled to the scapula 55. For example, a glenoid assembly 60 can be provided that includes a glenoid baseplate 62 to support the articular body 66. The glenoid baseplate 62 can be coupled with the scapula 55. The glenoid baseplate 62 can have an anchor peg 64 configured to be advanced into the scapula 55. The glenoid baseplate 62 can have an end disposed on bone beneath the glenoid 58 if the glenoid 58 is reamed. In some embodiments described below the glenoid baseplate 62 can be placed on the glenoid 58 without or with minimal reaming.

In a sub-optimal case, the glenoid baseplate 62 is not properly placed on the scapula 55. FIGS. 1 and 2 show that the anchor peg 64 of the glenoid baseplate 62 can be placed into the scapula 55 in a sub-optimal manner in which a medial end of the anchor peg 64 pierces the posterior surface 78 of the scapula 55. The anchor peg 64 can be exposed outside the scapula 55 in that case. FIG. 2 shows that the medial end of the anchor peg 64 can pierce the anterior surface 76 or the posterior surface 78 of the scapula 55 These outcomes are sub-optimal for several reasons. The security of the connection between the anchor peg 64 and the bone of the scapula 55 is a function of the length over which there is direct contact between these structures. The direct contact provides opportunities for bony ingrowth, providing security. No such ingrowth will occur along a length that is completely exposed. Further, an exposed end could cause irritation to soft tissue around the scapula 55. Further, if the anchor peg 64 were to perforate the bone in an undesirable location the perforation could weaken the scapula and increase the risk of fracture.

Figure 1A:
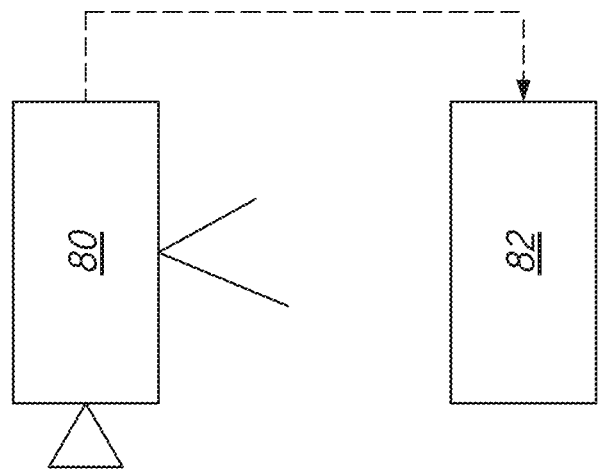
FIG. 1A is a schematic view of a glenoid and an imager that can be used to gather imaging information pertaining to the glenoid.
Figure 1A:
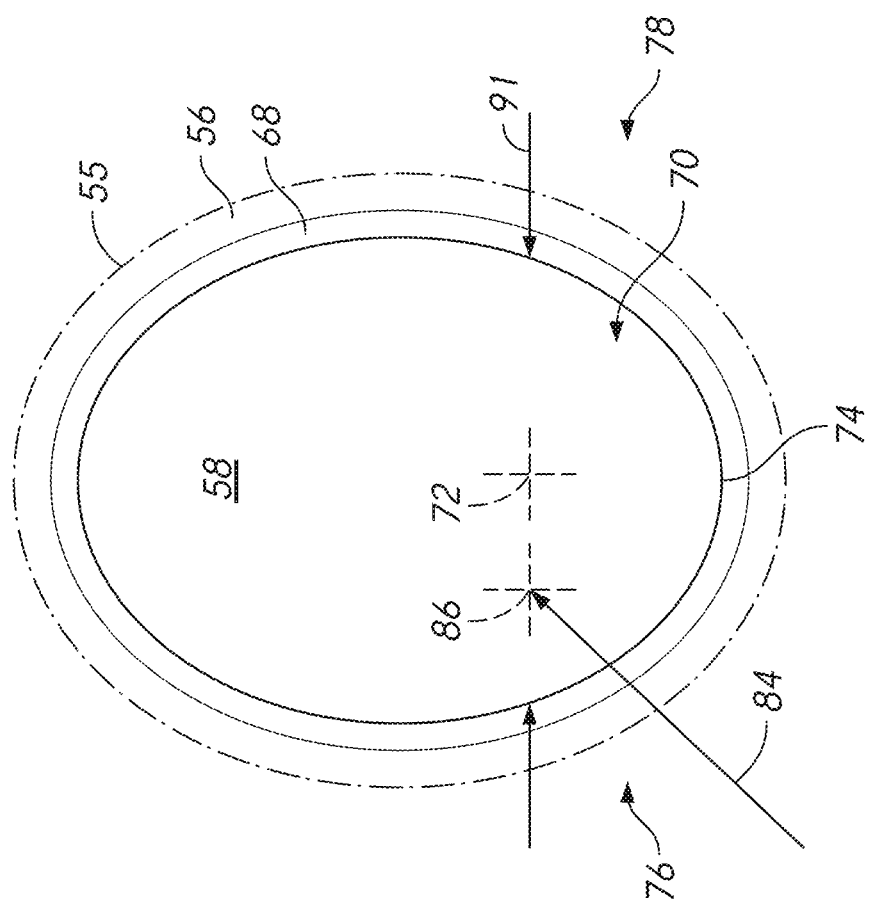
Figure 2:
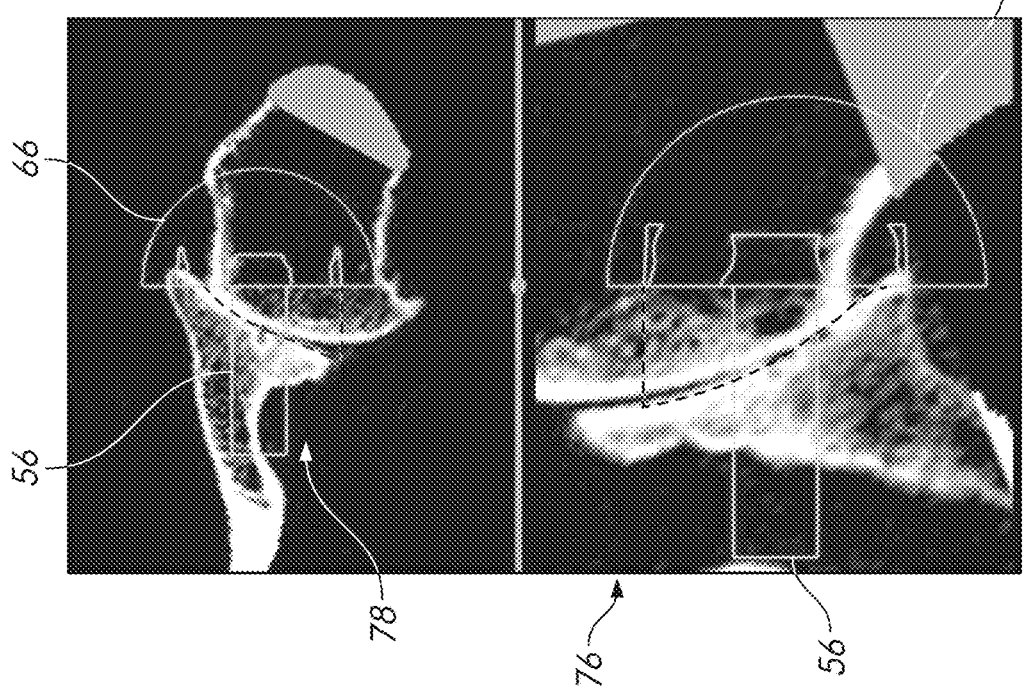
FIG. 2 shows two views of a scapula with an articular assembly baseplate coupled thereto, a medial end of the baseplate projecting through posterior and anterior walls of scapulae.

FIG. 1A shows a schematic of a lateral side of a scapula 55. The glenoid 58 includes an articular surface separated from the rest of the glenoid 58 by a glenoid rim 68. A healthy shoulder joint will generally have within the glenoid rim 68 an elongate articular surface that has a generally circular inferior portion 70. More particularly the inferior portion 70 can be bounded by a circular segment of the glenoid rim 68. The circular portion of the glenoid rim 68 can be disposed about a center 72. More generally, the center 72 can be a central portion, e.g., a geometric center, of the inferior portion 70. The center 72 can be disposed on or along a infero-superior axis of the glenoid rim 68 that extends from the superior-most portion (located at the top of the graphic in FIG. 1A) of the glenoid rim 68 to the inferior-most portion (located at the bottom in FIG. 1A) of the glenoid rim 68. The center 72 may be located at a central portion, e.g., a mid-point, of a chord extending across the glenoid rim 68 at an infero-superior position disposed inferior of a geometric center of the entire glenoid 58 or glenoid rim 68. For example, the center 72 can be located about one-half to two-thirds of the distance from the inferior-most point of the glenoid rim 68 to the geometric enter of the entire glenoid 58 or glenoid rim 68.

As will be discussed in greater detail below, an imager 80 can be used to scan the scapula 55 to gather imaging information. That information can be processed in an image processing system 82. The image processing system 82 can include a memory that can store imaging information corresponding to scanned data from the imager 80. The image processing system 82 can also include one or more hardware processors that can execute instructions. The image processing system 82 can process the imaging information to identify all the foregoing structures of the scapula 55. The imaging information can also be processed to locate an anchor trajectory 84 in a direction into the scapula 55 for placement of an anchor peg. The anchor trajectory 84 can be a direction from a blind hole 220 (discussed below in connection with FIG. 7A) in the lateral surface 56 of the scapula 55. The blind hole 220 can extend from an opening 224 (shown schematically in FIG. 1A as the opening 86) along the anchor trajectory 84. The anchor trajectory 84 can be offset from the center 72 of an inferior portion 74 of a glenoid 58. As shown in FIG. 1A the offset can be in the direction of the anterior surface 76. The opening 86 can be located between the center 72 and the anterior surface 76. The opening 86 can be located 10% of the distance from the center 72 to the anterior aspect of the glenoid rim 68 adjacent to the anterior surface 76 of the scapula 55. The opening 86 can be located 20% of the distance from the center 72 to the anterior aspect of the glenoid rim 68 adjacent to the anterior surface 76 of the scapula 55. The opening 86 can be located 30% of the distance from the center 72 to the anterior aspect of the glenoid rim 68 adjacent to the anterior surface 76 of the scapula 55. The opening 86 can be located 40% of the distance from the center 72 to the anterior aspect of the glenoid rim 68 adjacent to the anterior surface 76 of the scapula 55. The opening 86 can be located 50% of the distance from the center 72 to the anterior aspect of the glenoid rim 68 adjacent to the anterior surface 76 of the scapula 55. The opening 86 can be located 60% of the distance from the center 72 to the anterior aspect of the glenoid rim 68 adjacent to the anterior surface 76 of the scapula 55. In some cases, the opening 86 is located in a direction other than toward the anterior surface 76, e.g., closer to the posterior surface 78 of the scapula 55 by any of these or other percentages. The opening 86 could be in other directions as well, e.g., inferior, superior, or some direction between any of anterior, posterior, inferior, or superior depending on the needs of the patient.

Figure 1C:
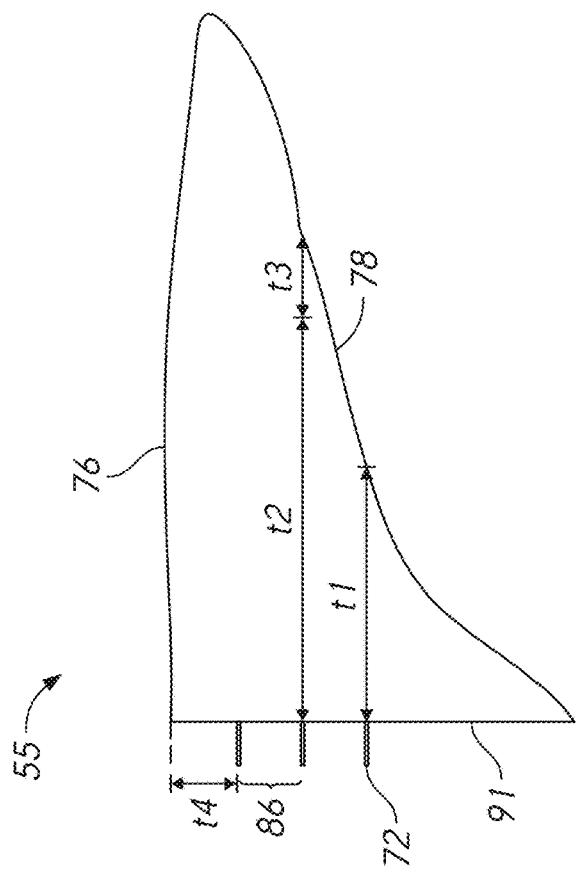
FIG. 1C is a schematic diagram of a portion of a scapula including a glenoid.
Figure 1B:
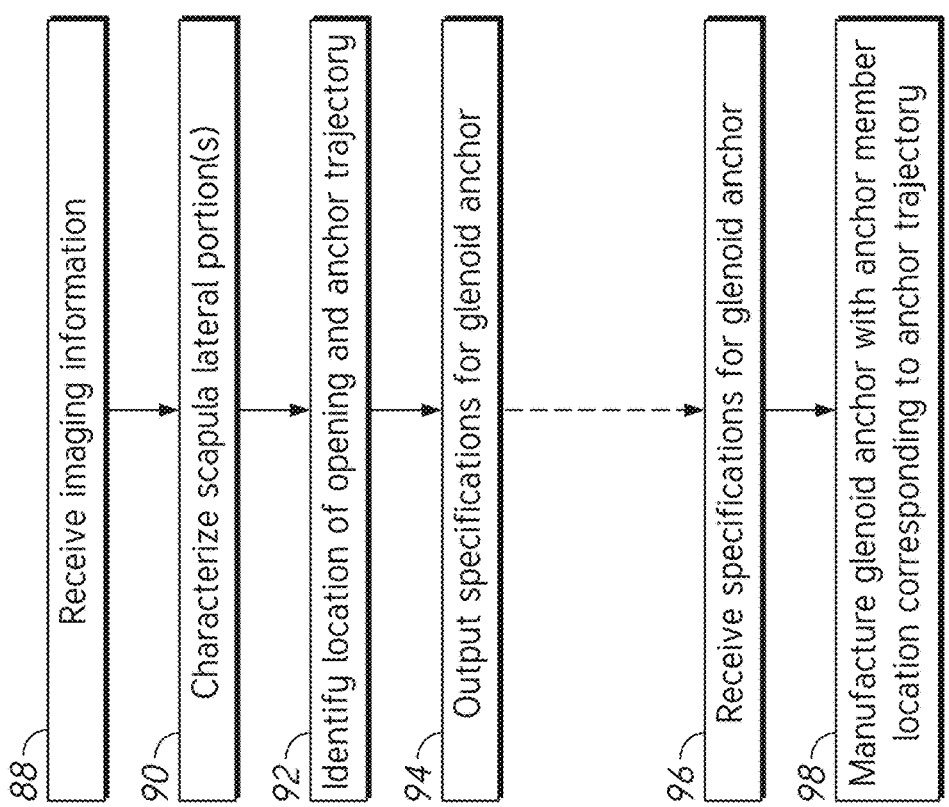
FIG. 1B is a flow chart of a method that can be performed with imaging information.

The image processing system 82 can be configured to process imaging information in any suitable manner. FIG. 1B shows one method that can be performed at least in part by the image processing system 82. In a step 88 a process can receive the imaging information. For example, the imager 80 can be connected by a network to a computer having a processor configured to receive the imaging information. The network can include an Internet connection, a wireless or wired connection within the same facility where the imager 80 is located. In some applications, a data file including the imaging information can be physically transported to an image processing computer. In some applications, the imager 80 is directly connected to a computer with a processor configured to process the imaging information.

Thereafter in a step 90 a lateral portion or surface 56 of a scapula 55 can be characterized. The characterization of the lateral portion can include segmentation to create a virtual model of all or a portion of the scapula 55. The step 90 can include forming a virtual model of all or a portion of the humerus 50. The step 90 can include forming a virtual model of all or a portion of the glenoid 58. A virtual model formed in step 90 can include a model of the glenoid rim 68. The virtual model formed in step 90 can include a model of an inferior portion 70 of the glenoid rim 68. In step 90, the center 72 of the inferior portion 70 can be identified in the virtual mode. The glenoid 58 can be characterized to locate the center 72, e.g., by obtaining a radius of curvature of the inferior portion 70. The center 72 can be identified as the center for a radius of curvature of the inferior portion 70.

The step 90 can include characterizing a lateral surface 56 of the scapula 55. The scapula 55 can be disposed in the immediate vicinity of the glenoid 58, e.g., lateral facing bone disposed around the glenoid 58. In some cases, the scapula 55 is further characterized medially of the lateral surface 56, e.g., along an anterior surface 76 and/or along a posterior surface 78 of the scapula 55. The step 90 can include determining the thickness of the scapula 55 between the anterior surface 76 and the posterior surface 78 at one or more locations of the glenoid 58. For example, thicknesses can be determined along the line 91 as shown in FIGS. 1A and 1C. FIG. 1C provides a simplified illustration of the line 91 as a straight line. In most examples of the glenoid 58 the line 91 follows the curvature of the glenoid 58, e.g., having a concavity facing laterally. The line 91 can extend from an anterior side of the glenoid rim 68 to a posterior side of the glenoid rim 68. A thickness t1 can be determined as a distance extending medially from the center 72. The distance can be measured perpendicular to a tangent line of the glenoid 58 at the center 72.

The step 90 can also include determining a thickness t2 at a location spaced apart from the center 72 if the thickness t1 is not sufficient to fully contain the anchor peg 64 of a glenoid baseplate 62. The location of the opening 86 can be determined as a location where the sum of a thickness t2 and a thickness t3 exceed a threshold. In one method, it is preferred to provide the thickness t2 from the end of a blind hole 220 that can be formed to retain the anchor peg 64 to the exterior wall of the posterior surface 78. For example, the thickness t3 can be at least large enough to leave the cortical wall at the posterior surface 78 intact. In one technique, the thickness t3 is measured from a portion of the blind hole 220 that is closest to the nearest wall of the scapula 55. For example if the posterior wall of the scapula 55 is sloped anteriorly in the vicinity of the end of the blind hole 220, the measurement for t3 would be from the posterior aspect of the blind hole 220 (rather than from the center of the blind hole) to the posterior wall.

FIG. 1C shows that in some cases, the scapula 55 can have a shape that allows the opening 86 to be placed over a range of positions. A distance from the location of the measurements thickness t2 and thickness t3 to the location of a measurement of a thickness t4 from the anterior surface 76 of the scapula 55 provides a range of possible locations for the opening 86. Upon identification of the range of positions for the opening 86, selection of the location of the opening 86 can be based on other factors such as bone quality below the glenoid 58 along the range of positions show in FIG. 1C. In some methods, the presence and location of any deformity can be considered. For example, the presence and location of a deformity can impact the ability of peripheral screws to be secured to the bone. So, the location of the opening 86 can be adjusted or selected to provide the best overall anchorage including that provided by peripheral screws.

The image processing system 82 can perform the step 92 in which the location of the opening 86 and the anchor trajectory 84 are determined. The image processing system 82 can determine the dimensions t2 and t3 as a part of determining the location of the opening 86 and the anchor trajectory 84. For example, a hardware processor in the image processing system 82 can execute code implementing a method that determines the thicknesses t2 and t3 for a given location offset from the center 72. At a location disposed an incremental distance anteriorly from the center 72, the image processing system 82 can determine the dimension t3. The thickness t3 can provide an anatomic reference distance, such as the thickness of the cortical wall adjacent to the anterior or posterior wall of the scapula beneath the glenoid (see FIG. 1C). The thickness t2 can be determined by the image processing system 82 from glenoid surface and the thickness t3 (see FIG. 1C). If the thicknesses t2 and t3 are sufficient for a given patient, the anchor trajectory 84 as well as the location for the opening 86 can be established. If either thickness t2 or t3 is not sufficient, a further increment from the center 72 can be evaluated by the image processing system 82. The condition at the bone corresponding to this further increment, e.g., the thicknesses t2 and t3, can be evaluated by the image processing system 82 to determine if the thicknesses t2 and t3 are sufficient. In some embodiments the image processing system 82 performs additional steps of the method of FIG. 1B, e.g., to generate a configuration for a glenoid baseplate 62. The configuration of the glenoid baseplate 62 can include an amount of offset between a center of a proximal or distal (or lateral or medial) portion of the glenoid baseplate 62 and the location of the center of the anchor peg 64. The direction along which the anchor peg 64 extends can be generally perpendicular to a lateral or medial surface of the glenoid baseplate 62 in some embodiments. In some methods, the image processing system 82 concludes the step 92 upon determining the location of the opening 86 and the corresponding position of the anchor peg 64 as well as the anchor trajectory 84 within the scapula 55 and the corresponding configuration (e.g., orientation and length) of the anchor peg 64. The opening 86 may advantageously be determined to be located anterior of the center 72, posterior of the center 72, inferior of the center 72, superior of the center 72, or any combination of anterior, posterior, inferior and superior to the center 72 as needed based on the analysis in step 90.

FIGS. 1 and 1C shows that the direction of the opening 86 relative to the center 72 is toward the anterior surface 76. The opening 86 could be located between the center 72 and the posterior surface 78, as shown in FIG. 2. A range of positions for the opening 86 between the center 72 and the posterior surface 78 also can be provided if the posterior surface 78 extends more generally medially-laterally and the anterior surface 76 is more curved toward the posterior surface (as in the lower image of FIG. 2).

In a step 94, a specification or configuration for a glenoid baseplate 62 can be output. The output can be in the form of drawings. The output can be computer code to be used by a rapid manufacturing facility. The output in step 94 can be sent directly or indirectly to multiple recipients, including a review recipient, a manufacturing recipient, a physician customer and/or a patient customer.

In step 96 the configuration or specifications output in step 94 can be received by a manufacturing facility. The configuration or specification can be received by other parties in the step 96. The step 96 can involve a 3D printer of any sort to receive instructions output in the step 94. The instructions can be received and can be implemented by the 3D printer forming the glenoid baseplate 62 in a step 98. The step 98 generate the glenoid baseplate 62 by forming the glenoid baseplate 62 and thereafter putting the glenoid baseplate 62 through appropriate finishing processes. The step 98 can include transferring the glenoid baseplate 62 to the surgeon immediately upon concluding the method of FIG. 1B or subsequently.

Figure 1E:
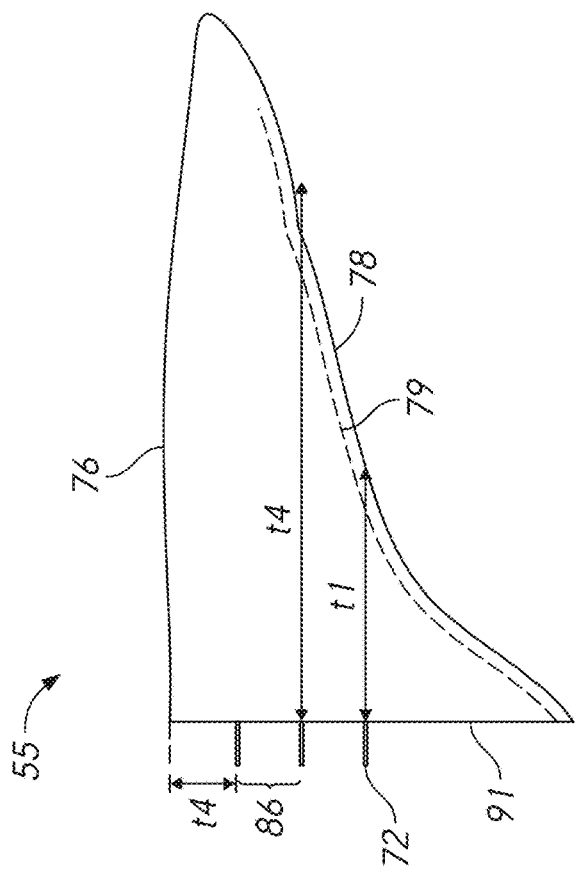
FIG. 1E is a schematic diagram of a portion of a scapula including a glenoid.
Figure 1D:
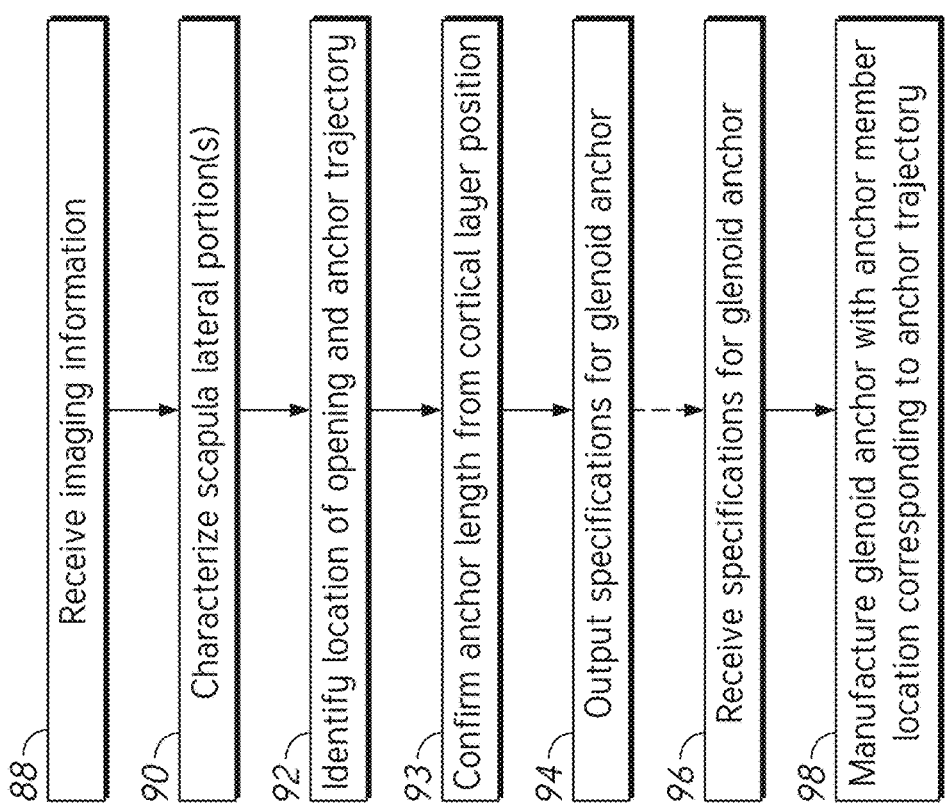
FIG. 1D is a flow chart of a method for providing for bi-cortical fixation while achieving sufficient anchor peg length.

FIGS. 1D-1E illustrate further variations of methods and apparatuses herein. The method illustrated in FIG. 1D is similar to that of FIG. 1B except that there is an additional step 93 in which the length of an elongate body, e.g., an anchor peg, which may be described as an anchor length, is confirmed. An anchor length can correspond to a thickness t4 between a glenoid surface. In one technique the determination of the thickness t4 can include using the image processing system 82 to identify a cortical boundary 79, e.g., a location where generally cancellous bone transitions to generally cortical bone. The thickness t4 can be required to be at least the distance from the glenoid surface to the cortical boundary 79. The thickness t4 can be required to be greater than this distance, such that the result is that a glenoid baseplate formed with an elongate body defined by the method of FIG. 1D reaches and in some cases extends through the scapula wall to provide bi-cortical fixation. The rest of the method of FIG. 1D can be the same as the method of FIG. 1B.

A patent application filed under U.S. Provisional Application No. 62/847,100 on May 13, 2019 listing inventors Pierric Deransart and Vincent Simoes and bearing to title Patient-Matched Orthopedic Implant is hereby incorporate by reference herein in its entirety for further disclosure of various methods related to configuring and making various embodiments of glenoid baseplates and other orthopedic implants in a patient specific or patient-matched manner and for further disclosure of such glenoid baseplates and orthopedic implants as well as for all other purposes.

Figure 3:
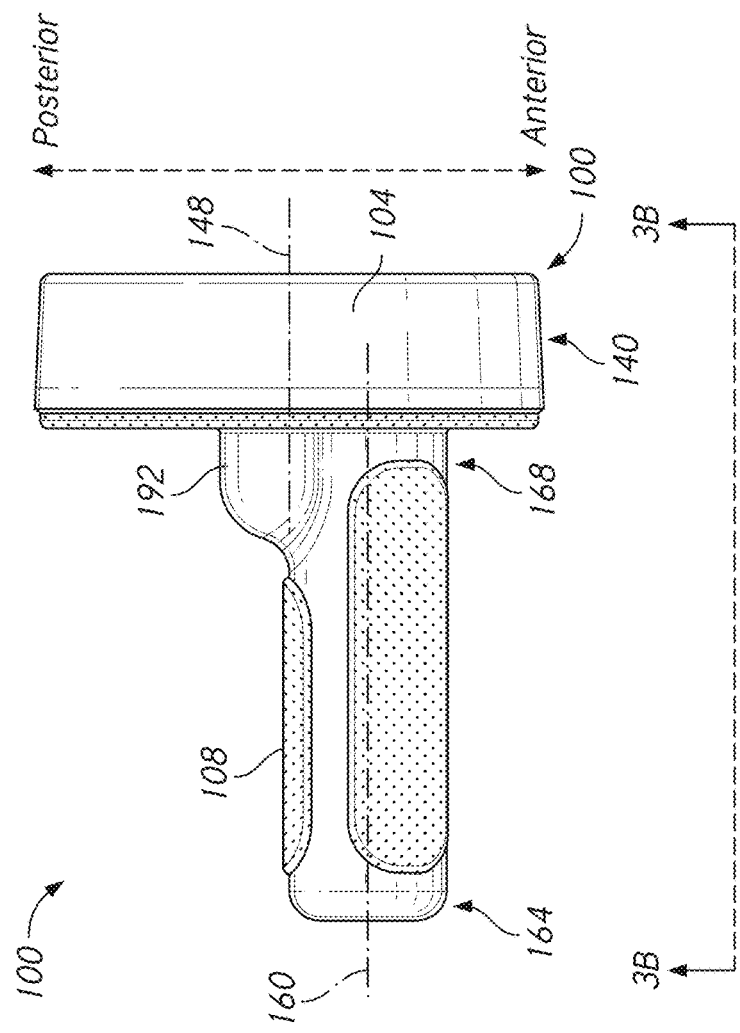
FIG. 3 is a side view of one embodiment of a glenoid baseplate having an anteriorly offset anchor peg.
Figure 3A:
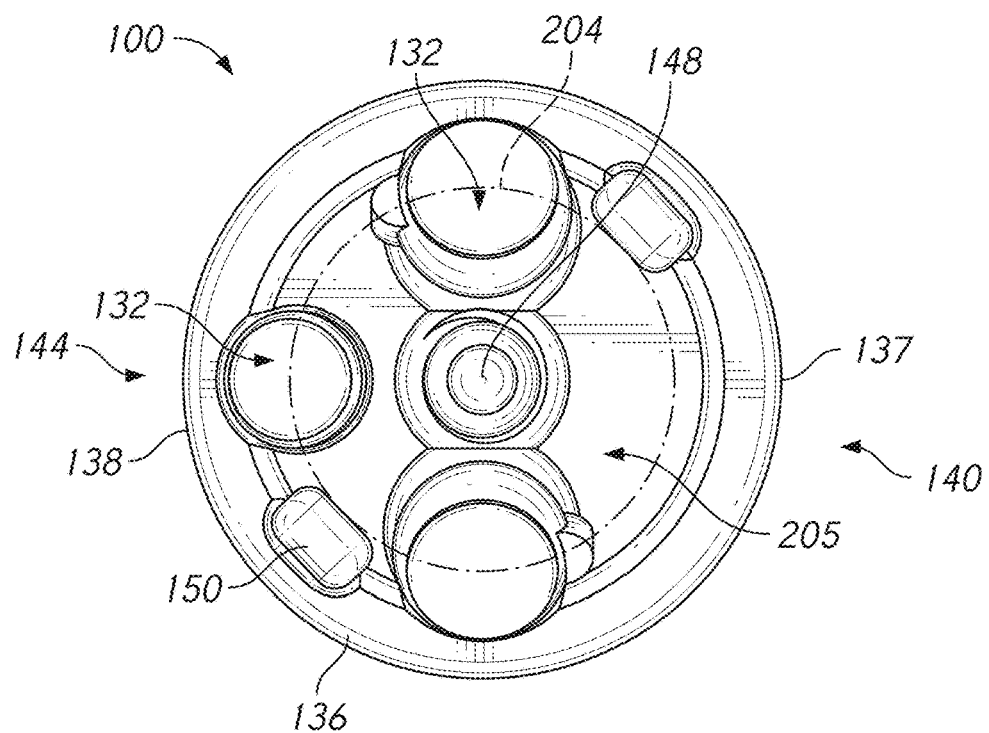
FIG. 3A is a lateral side view of the glenoid baseplate of FIG. 3.
Figure 3B:
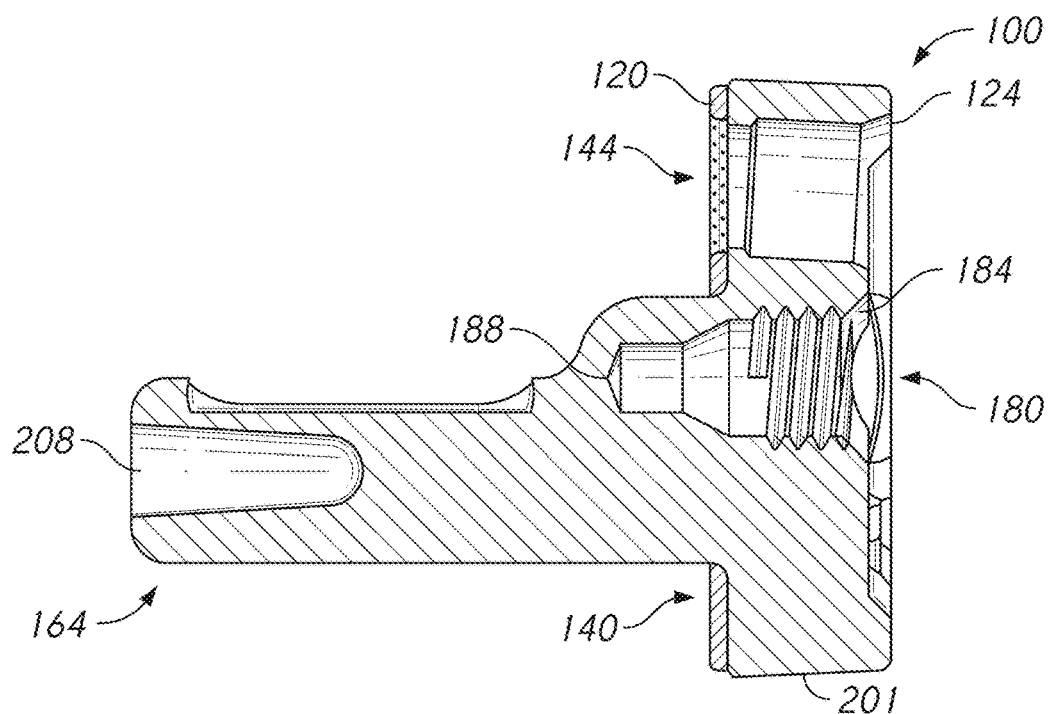
FIG. 3B is a cross-section of the glenoid baseplate of FIG. 3.

FIGS. 3-3B shows an example glenoid baseplate 100 according to one embodiment. The glenoid baseplate 100 can be used to secure a glenoid articular member to a glenoid as discussed below. The glenoid baseplate 100 is an example of an implementation of the glenoid baseplate 62 discussed above.

The glenoid baseplate 100 includes a transverse body 104 and an elongate body 108. The elongate body 108 can be configured as an anchor peg, e.g., similar to the anchor peg 64. The glenoid baseplate 100 includes a first side 120. The first side 120 can be a medial side configured to engage scapula bone of a patient. The glenoid baseplate 100 includes a second side 124. The second side 124 can be a lateral side configured to face away from the medial side 120. The second side 124 can face away from the scapula 55 when the first side 120 is secured against the scapula 55.

FIG. 3A shows that the glenoid baseplate 100 can include plurality of anchor apertures 132, which can be a plurality of bone screw holes, formed between the medial side 120 and the lateral side 124. The anchor apertures 132 can be evenly distributed about the transverse body in some embodiments. In some embodiments, there is an uneven distribution of the anchor apertures 132 about the second side 124. The anchor apertures 132 can be fixed holes or fixed passages through the baseplate 100. The anchor apertures can be formed as holes or passages defined in part by or through internal members that are disposed within recesses in the baseplate 100. In some embodiments, the recesses and/or apertures 132 in the baseplate 100 can include a non-threaded and/or threaded surface. In various examples one or more of two or more apertures 132 can be threaded and another one or more of the two or more apertures 132 can be non-threaded. In an example, two threaded apertures 132 can be disposed through an augmented portion of the first or medial side 120, e.g., an angled surface thereof, and one or more, e.g., two, non-threaded holes can be disposed adjacent to the threaded holes. The augmented portion can be a pre-defined augment appropriate for the patient or can be a patient-specific augmented portion that is designed specifically for the patient based on imaging of the scapula and/or glenoid region of the patient. In some embodiments, the internal member(s) can include a semi-spherical outer surface and can be disposed in a recess that is semi-spherical, in order to permit movement, e.g., rotation, tilting and/or swiveling, of the internal member with respect to the baseplate 100. The internal member(s) allow an orientation of bone anchors relative to the baseplate 100 to be selected at the time of a surgery. Further details of internal members that can tilt, rotate or swivel are described in U.S. Pat. No. 9,629,725B2, which is hereby incorporated herein by reference.

The glenoid baseplate 100 can have a circular periphery 136 that can extend between the medial side 120 and the lateral side 124. The circular periphery 136 can be tapered, e.g., larger toward the first side 120 than toward the second side 124. The circular periphery 136 can correspond to a curvature of an inferior portion 74 of a glenoid rim 68 of the scapula 55. The elongate body 108 can be disposed within the circular periphery 136 at a location to be aligned with the anchor trajectory 84 when the periphery is aligned with the curvature of the inferior portion 74 of the glenoid rim 68. The elongate body 108 can be aligned with the opening 86 by rotationally orienting the glenoid baseplate 100, e.g., by orienting an indicia of directionality as directed. A notation such as "SUP" can be marked on the transverse body 104 to be aligned with the superior direction. Other indicia of directionality can be provided in other embodiments.

FIG. 3A shows that the circular periphery 136 of the glenoid baseplate 100 can have a center 148 with a feature for securing an articular body to the glenoid baseplate 100 as discussed further below. The circular periphery 136 can have an anterior periphery 137 comprising a portion of the circular periphery 136. The circular periphery 136 can have a posterior periphery 138. The posterior periphery 138 comprises a posterior portion of the circular periphery 136. The elongate body 108 can be configured as a projection that extends from the medial side 120. The projection 108 can be located closer to the anterior periphery 137 than to the posterior periphery 138.

The glenoid baseplate 100 can include an anterior portion 140 configured to be oriented toward an anterior side of a scapula 55. The glenoid baseplate 100 can include a posterior portion 144 configured to be oriented toward a posterior side of the scapula 55. The anterior portion 140 and the posterior portion 144 can disposed around, e.g., can surround the center 148.

FIG. 3 shows how the transverse body 104 and the elongate body 108 can be secured or coupled to each other. The elongate body 108 can extend along a longitudinal axis 160. The elongate body 108 can have a first end 164 and a second end 168. The second end 168 can be coupled with the first side 120 (e.g., with the medial side) of the transverse body 104. The first end 164 can be disposed away from the second end 168 (e.g., away from the lateral end). The first end 164 can be a medial end 164 of the glenoid baseplate 100. The longitudinal axis 160 of the anchor peg 108 is off-set from the center 148 of the circular periphery 136 toward the anterior portion 140. The center 148 is illustrated by a dashed line in FIG. 3. FIGS. 3A and 3B show that a recess is formed at the center 148. The recess allows a connection feature (e.g., a screw) to be used to secure an articular body (such as the articular body 66) to the glenoid baseplate 100. The configuration of the glenoid baseplate 100 allows the connection between the articular body 66 and the glenoid baseplate 100 to be along the center 148 while allowing the location of the elongate body 108 to be spaced apart from the center 148, e.g., according to the method of FIG. 1B.

FIGS. 3A and 3B show that the glenoid baseplate 100 can have a threaded hole 180 to facilitate connection of an articular body (e.g., the articular body 66) to the glenoid baseplate 100. The threaded hole 180 preferably is configured as a blind hole with an open end 184. The blind hole configuration can include an enclosed end 188. The enclosed end 188 greatly increases the strength of the glenoid baseplate 100 compared to where the threaded hole 180 would open up on the medial side of the structure. The threaded hole 180 can be formed within a fastener body 192. The fastener body 192 can be configured as a transverse extension of the elongate body 108 as seen most prominently in FIG. 3. The fastener body 192 can have a width that is less than the diameter of the elongate body 108 at the first end 164 thereof. The fastener body 192 can extend by a distance that is less than the medial-lateral thickness of the transverse body 104. The fastener body 192 can include a first end 194 and a second end 196. The second end 196 can be coupled with the first side 120 of the transverse body 104. The first end 194 can be disposed away from the transverse body 104. The fastener body 192 enables the fastener to extend by at least a small distance beyond the transverse body 104. This configuration allows the transverse body 104 to be relatively or completely flat on the second side 124.

The circular periphery 136 of the transverse body 104 comprises a tapered profile 201 configured to mate with a tapered recess of the articular body 66. The second side 124 of the glenoid baseplate 100 can have an aperture circumference 204 wherein the anchor apertures 132 are evenly distributed about the lateral face of the transverse body 104. FIG. 4A shows an embodiment where all of the anchor apertures 132 are evenly spaced about a lateral face of the transverse body 104. FIG. 3A shows that an anterior portion of an aperture circumference 204 opposite the elongate body being formed without an aperture, e.g., providing a continuous area 205. The continuous area 205 can include a solid surface at a regular spacing from adjacent anchor apertures 132. The presence of a continuous area 205 can arise due to the shifting of the position of the elongate body 108 into the area of the anchor apertures 132. Because the elongate body 108 is solid there is not an opportunity to direct a bone screw through that area. Therefore, the continuous area 205 can be provided. The continuous area 205 can be a solid or unperforated area.

In some embodiments, a medial interface 208 is provided in the first end 164 of the elongate body 108. The medial interface 208 can include a blind hole that is centered on the distal face of the elongate body 108. The medial interface 208 could be used to secure patient bone matter or graft matter. A blind hole allows a pin or peg to be inserted into the elongate body 108 during handling or processing of the glenoid baseplate 100. During such holding the glenoid baseplate 100 can be further processed to provide appropriate smoothed surfaces. The handling interface 208 is optional and can be replaced with a solid surface at the second end 168 of the elongate body 108.

Handling of the glenoid baseplate 100 can be facilitated by providing a tooling interface 150 on the transverse body 104, e.g. on the second side 124 thereof. As discussed above, the second side 124 can be a lateral side of the glenoid baseplate 100. The second side 124 can be accessible by a tool that can extend through the skin to the surgeon in use when the tool has been used to place the glenoid baseplate 100 through the skin toward the glenoid. The tooling interface 150 can include two or more opposed slots, openings or blind holes in the second side 124 of the transverse body 104. The slots, openings or blind holes can be angled toward each other such that the ends thereof are closer to each other than are the ends of the slots, openings or blind holes at the surface of the second side 124. As shown, the tooling interface 150 can be disposed just outside of the aperture circumference 204 between two circumferentially adjacent anchor apertures 132.

Figure 4:
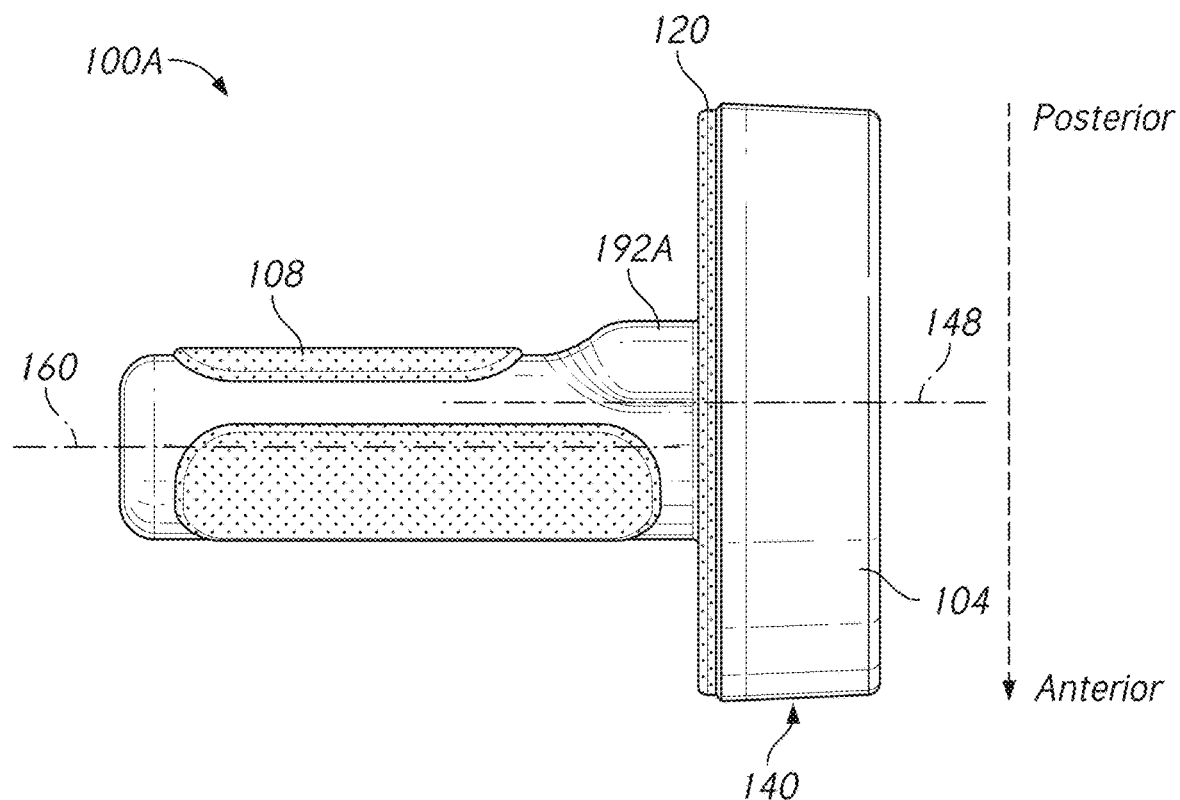
FIG. 4 is side view of another embodiment of a glenoid baseplate having anteriorly offset anchor peg.
Figure 4A:
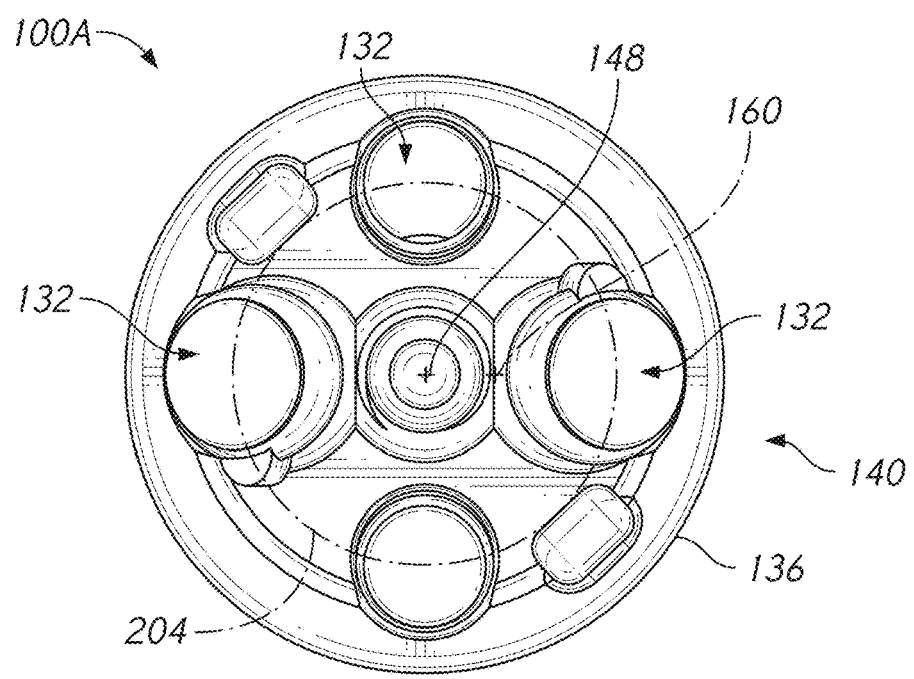
FIG. 4A is a lateral side view of the glenoid baseplate of FIG. 4.

FIGS. 4 and 4A show a glenoid baseplate 100A that is similar to the glenoid baseplate 100 except as described differently below. The description of the glenoid baseplate 100 supplements the description of the glenoid baseplate 100A. Any features of the glenoid baseplate 100A that are compatible with the glenoid baseplate 100 also supplement to the glenoid baseplate 100. The glenoid baseplate 100A includes the transverse body 104 and the elongate body 108 as discussed above. The elongate body 108 extends along the longitudinal axis 160. The transverse body 104 can have a circular periphery 136 with a center 148. An offset between the center 148 and the elongate body 108 can be provided. The offset can be in the anterior direction, as shown in FIG. 4. Depending on the nature of the scapula to which the glenoid baseplate 100A is to be applied the offset between the elongate body 108 and the center 148 can be in another direction, e.g., in the posterior direction. The offset between the elongate body 108 and the center 148 can be in other directions as well, e.g., inferior, superior, or some direction between any of anterior, posterior, inferior, or superior depending on the needs of the patient.

The glenoid baseplate 100 can have a fastener body 192A that is disposed alongside the elongate body 108. The fastener body 192A can be similar to the fastener body 192. For instance, the fastener body 192A can have an enclosed end 188 and an open end 184. The fastener body 192 can have a threaded hole 180 that extends from the open end 184 to the enclosed end 188. The fastener body 192A can be provided to allow at least a portion of a fastener coupled to the glenoid baseplate 100A to be disposed below a bone surface to which the first side 120 is applied. The fastener coupled to the fastener body 192A can extend out of the open end 184 and into an articular body to additionally secure the reverse articular body 66 to the glenoid baseplate 100A. Accordingly, a portion of a fastener can be disposed in the reverse articular body 66, a portion in the thickness of the transverse body 104 and a portion in the fastener body 192A.

The fastener body 192A extends away from a side surface of the elongate body 108 by a lesser extent than doe the fastener body 192 in the glenoid baseplate 100. Placement of the glenoid baseplate 100A requires less preparation of the bone of the glenoid 58 to accommodate the lesser volume of the fastener body 192A compared to the fastener body 192. Also, the location of the elongate body 108 closer to the fastener body 192A allows the periphery of the elongate body 108 to be disposed inward of the anchor apertures 132 in the transverse body 104. FIG. 4A shows that the configuration allows the aperture circumference 204 to include anchor apertures 132 that are evenly distributed entirely around the transverse body 104. For example, the transverse body 104 can have anchor apertures 132 located between the position of the elongate body 108, e.g., of the longitudinal axis 160, and the anterior portion 140 of the circular periphery 136. The glenoid baseplate 100A advantageously enables the elongate body 108 to be lodged completely in bone medial of the first side 120 of the transverse body 104 and also allows anchors to be disposed through the anchor apertures 132 at an even distribution providing even securement to the scapula.

Figure 5:
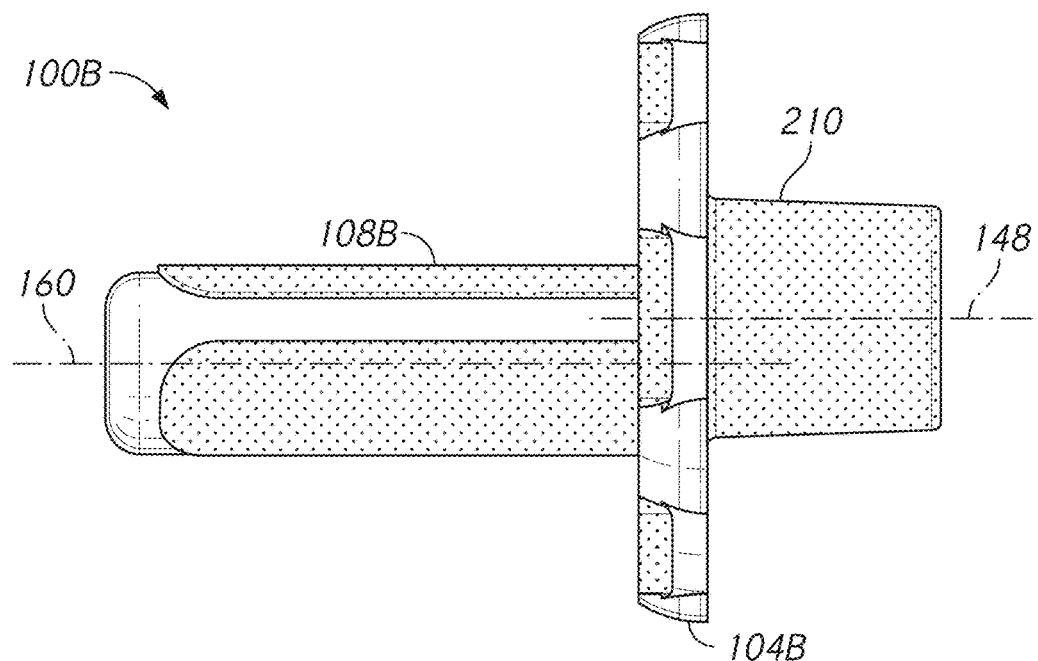
FIG. 5 is a side view of another embodiment of a glenoid baseplate having anteriorly offset anchor peg and a lateral mounting projection with a relatively small diameter taper.
Figure 5A:
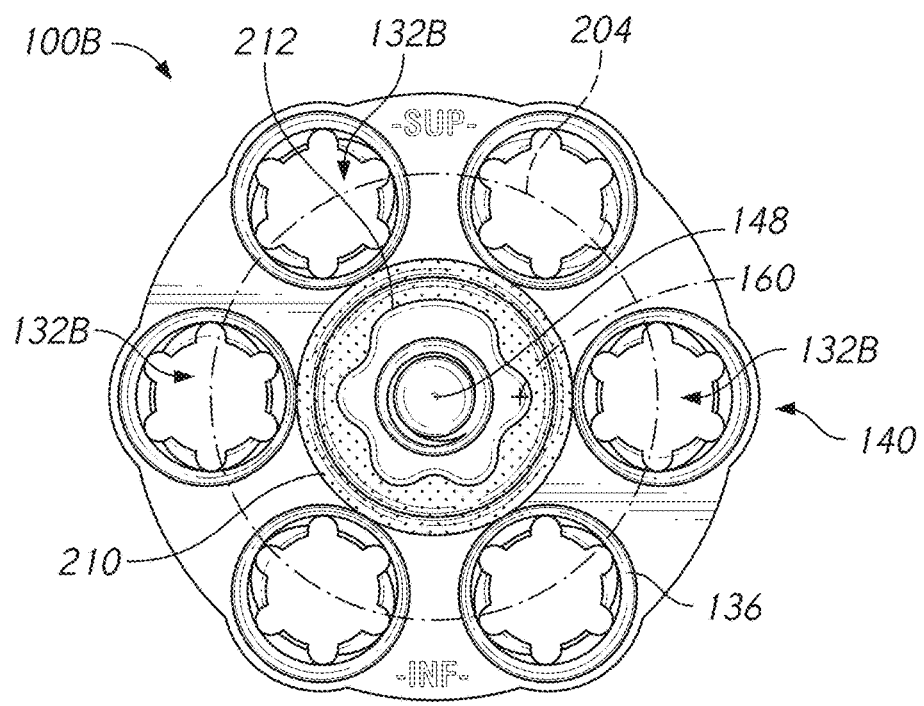
FIG. 5A is a lateral side view of the glenoid baseplate of FIG. 5.
Figure 5B:
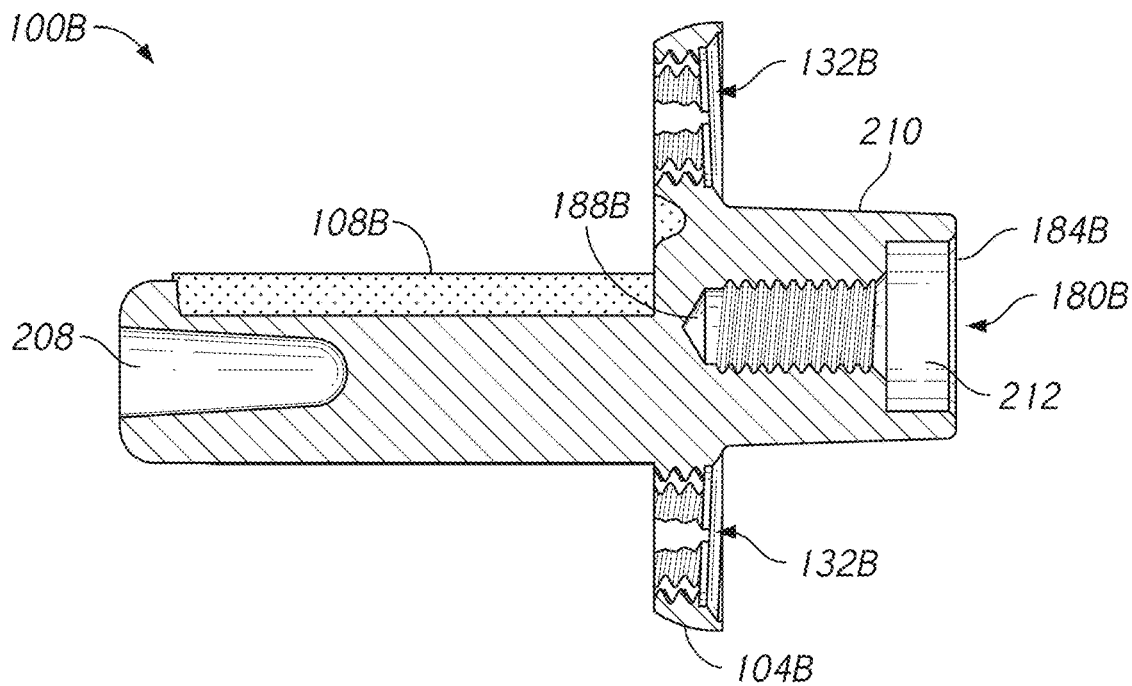
FIG. 5B is a cross-section of the glenoid baseplate of FIG. 5.

FIGS. 5-5B show a glenoid baseplate 100B that is similar to the glenoid baseplate 100 and the glenoid baseplate 100A except as described differently below. The descriptions of the glenoid baseplate 100 and the glenoid baseplate 100A supplement the description of the glenoid baseplate 100B. Any description of features of the glenoid baseplate 100B that are compatible with the glenoid baseplate 100 or the glenoid baseplate 100A also supplements that of the glenoid baseplate 100 and/or the glenoid baseplate 100A.

The glenoid baseplate 100B includes an elongate body 108B and a transverse body 104B. The elongate body 108B is disposed along a longitudinal axis 160. The transverse body 104B is symmetrical about a center 148, which is illustrated as a center axis 148. The glenoid baseplate 100B includes a coupling projection 210 disposed a side of the transverse body 104B opposite the elongate body 108B. The coupling projection 210 can be symmetrical about the center 148. The coupling projection 210 can have a tapered outer periphery. The coupling projection 210 can have an outer periphery that reduces in diameter along the length thereof from the transverse body 104B to a free end of the coupling projection 210. The coupling projection 210 can include a threaded hole 180B formed therein to engaged with the articular body 66. The threaded hole 180B can be disposed between an open end 184B and an enclosed end 188B within the coupling projection 210. The enclosed end 188B can be disposed within the thickness of the transverse body 104B. The enclosed end 188B can be disposed between the elongate body 108B and the coupling projection 210. A tooling interface 212 can be disposed in the threaded hole 180B. The tooling interface 212 can extend from the open end 184B toward the enclosed end 188B.

The tooling interface 212 can be rotationally asymmetric to contribute to visualizing or providing the correct orientation of the glenoid baseplate 100B relative to the scapula. For example, an arrangement of concavities can be provided about the tooling interface 212. An enlarged concavity can be provided at a superior portion of the tooling interface 212. The glenoid baseplate 100B also can be provided with visual indicia of orientation, e.g., labeled "SUP" for superior and/or "INF" for inferior on the lateral side of the transverse body 104B. In other embodiments, the transverse body 104B can be labeled "ANT" for anterior or "POS" for posterior. Other indicia could be used for indicating one or more of these orientations.

The transverse body 104B can include anchor apertures 132B that are similar to the anchor apertures 132 and can also include threads for connecting the transverse body 104B to bone anchor, e.g., screws, that can be advanced therethrough. The threads can be segmented to allow the threads to be secured to bone anchors in a fixed orientation, which orientation can be selected at the time of a surgery.

One advantage of the configuration of the glenoid baseplate 100B is that the elongate body 108B can have a cylindrical shape with a circular profile from a first end located at a first, bone-facing or medial side of the transverse body 104B to a second (medial) end of the elongate body 108B. The exterior surface of the elongate body 108B is free of a structure similar to the fastener body 192 or fastener body 192A because the faster advanced into the threaded hole 180B does not extend beyond the first, bone-facing or medial side of the transverse body 104B. This allows the preparation of the scapula bone of a patient to be simpler in that a circular hole can be formed in the recess allowing the glenoid baseplate 100B to be more easily inserted into the bone. The presence of the fastener body 192 or the fastener body 192A may require either supplemental preparation of the bone or compaction of the bone during impaction of the glenoid baseplate 100 or the glenoid baseplate 100A if the baseplate is prepared without a patient specific medial surface configured to be placed on the glenoid. In cases where the medial surface is made patient specific the fastener body 192 or the fastener body 192A may be located in an expanse of the baseplate that is augmented for the patient on the medial side of the baseplates and may be located laterally of the glenoid surface when applied. Thus, no additional bone preparation would be necessary for the fastener body 192 or the fastener body 192A.

The coupling projection 210 can provide a connection to the articular body 66 that is similar to the connection provided by the tapered profile 201 of the glenoid baseplate 100 or the glenoid baseplate 100A. The coupling projection 210 has a tapered profile that has larger dimensions toward the transverse body 104B than adjacent to the free end of the coupling projection 210. The largest dimension of the coupling projection 210 is smaller than the diameter of the side of the transverse body 104B to which the coupling projection 210 is coupled. Thus, the coupling projection 210 can be smaller than the transverse body 104B. The coupling projection 210 can have an aspect ratio that is greater than 1:5 (height to diameter of the projection 210). In various examples, the coupling projection 210 has an aspect ratio that is greater than 1:4, greater than 1:3, greater than 1:2, e.g., about 1:1. In contrast, the transverse body 104, the periphery of which provides the tapered profile 201 for mating to the articular body 66, can have an aspect ratio that is smaller than 1:1 (diameter to height of the body 104). The transverse body 104 can have an aspect ratio smaller than 1:2, smaller than 1:3, smaller than 1:4. In some example, the transverse body 104 has an aspect ratio that is between 1:2 and 1:7, e.g., about 1:5. The insertion and alignment of the articular body 66 with the smaller coupling projection 210 can be easier than the insertion and alignment of the articular body 66 over the generally larger tapered profile 201. The alignment of the body 66 to the smaller diameter projection 210 is easier in part because of the higher aspect ratio (length over width) of this feature. That is, the projection 210 is narrower and longer and thus has a much higher aspect ratio than the tapered profile 201, which is shorter and wider. The higher aspect ratio allows the articular body 66 to be placed over the free end of the coupling projection 210 and as it is advanced toward the transverse body 104B, the projection 210 guides the body 66 into the proper alignment prior to full connection. In the case of the tapered profile 201, the smaller aspect ratio provides less alignment confirmation by way of the structure of these features before the components are to be fully connected. With the presence of soft tissue and limited visibility the alignment is just more difficult. However, both interfaces provide excellent connection between the articular body 66 and the corresponding glenoid baseplate.

Figure 5C:
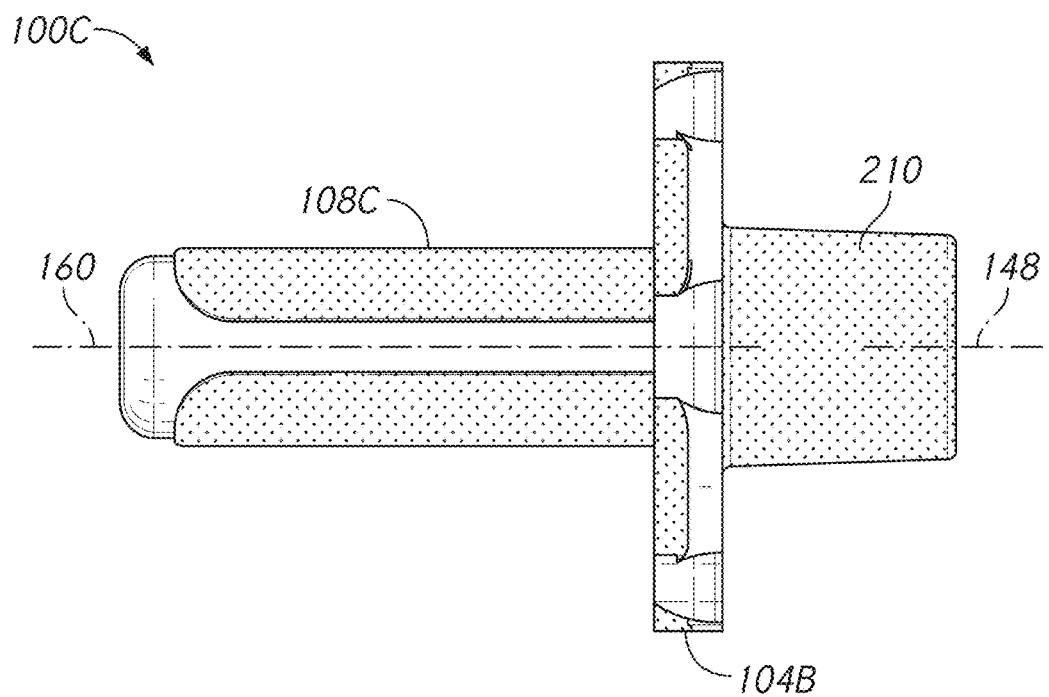
FIG. 5C is side view of another embodiment of a glenoid baseplate having a centered anchor peg.

FIG. 5C shows a glenoid baseplate 100C that is similar to the glenoid baseplate 100B except as described differently below. The glenoid baseplate 100C has similarity to some feature of the glenoid baseplate 100 and the glenoid baseplate 100A as well. The descriptions of the glenoid baseplates 100, 100A, 100B supplement the description of the glenoid baseplate 100C. Any description of features of the glenoid baseplate 100C that are compatible with the glenoid baseplates 100, 100A, 100B also supplements that of the glenoid baseplates 100, 100A, and/or the glenoid baseplate 100B.

FIG. 5C shows that the glenoid baseplate 100C has an elongate body 108C that is disposed on a medial side of the transverse body 104B. The transverse body 104B is disposed on the center 148 as in the glenoid baseplate 100B. The elongate body 108C is disposed along a longitudinal axis 160. The longitudinal axis 160 is aligned with, e.g., intersects or is colinear with the center 148 of the transverse body 104B. As such, the glenoid baseplate 100C provide a configuration in which both the coupling projection 210 and the elongate body 108C are symmetrical about a common axis. The glenoid baseplate 100C is suitable for patients with more symmetrical anterior surface 76 and posterior surface 78 and/or patients with thicker a scapula. These patients can receive the full length of the elongate body 108C along a direction perpendicular to a plane of the transverse body 104B extending away from the first side 120 of the transverse body 104B when the anchor trajectory 84 is aligned with the center 72 of the glenoid 58.

The configuration of FIG. 5C can have the coupling projection 210 and the tooling interface 212. The glenoid baseplate 100 can be formed with a symmetrical configuration similar to the glenoid baseplate 100C.

Figure 6:
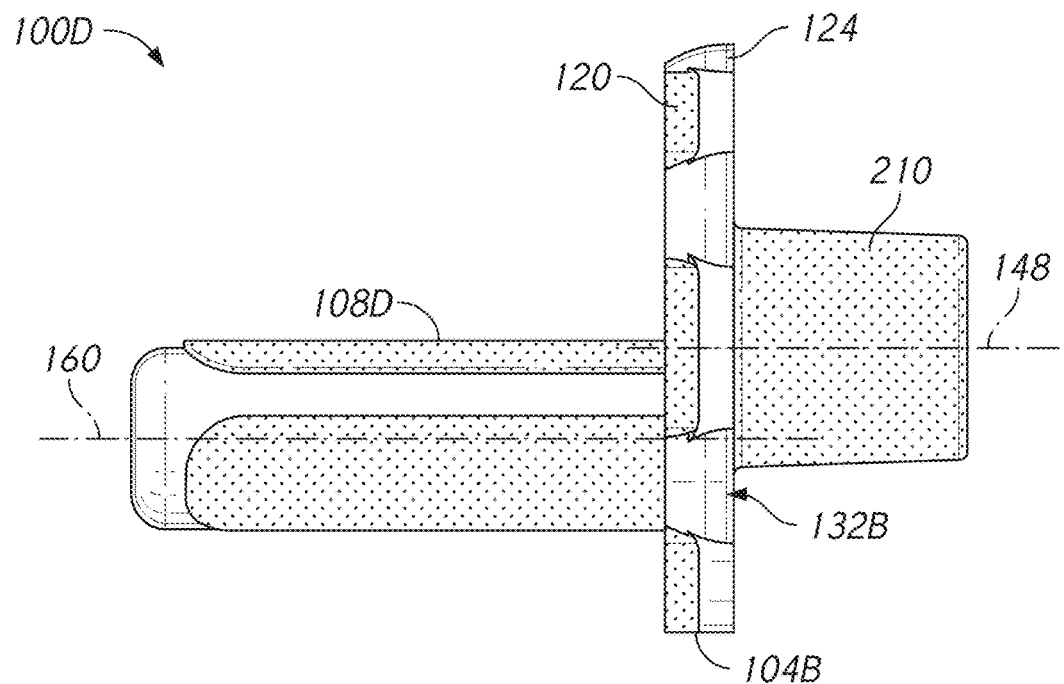
FIG. 6 is a side view of another embodiment of a glenoid baseplate having an anchor peg that is offset anteriorly to a position aligned with an aperture circumference.

FIG. 6 shows a glenoid baseplate 100D that is similar to the glenoid baseplates 100, 100B except as described differently below. The glenoid baseplate 100D has similarity to some feature of the glenoid baseplates 100A, 100C as well. The descriptions of the glenoid baseplates 100, 100A, 100B, 100C supplement the description of the glenoid baseplate 100D. Any descriptions of features of the glenoid baseplate 100D that are compatible with the glenoid baseplates 100, 100A, 100B, 100C also supplements that of the glenoid baseplate 100 and/or the glenoid baseplate 100, 100A, 100B, 100C.

The glenoid baseplate 100D has a transverse body 104B and an elongate body 108D. The elongate body 108D is similar to the elongate body 108B. The elongate body 108D extends from a first side 120 of the transverse body 104B to a free end disposed away from the first side 120. The elongate body 108D extends along a longitudinal axis 160. The longitudinal axis 160 can be offset from a center 148 of a coupling projection 210 disposed on a side of the transverse body 104B opposite to the elongate body 108D. The offset between the center 148 and the longitudinal axis 160 can be in an anterior direction. Such an offset will accommodate a patient where more bone stock is available toward the anterior surface 76 than toward the posterior surface 78 of the scapula 55.

The offset between the longitudinal axis 160 and the center 148 of the glenoid baseplate 100D or the glenoid baseplate 100 can be about 6 mm in one embodiment. The offset between the longitudinal axis 160 and the center 148 of the glenoid baseplate 100D or the glenoid baseplate 100 can be about 5 mm in one embodiment. The offset between the longitudinal axis 160 and the center 148 of the glenoid baseplate 100D or the glenoid baseplate 100 can be about 4 mm in one embodiment. The offset between the longitudinal axis 160 and the center 148 of the glenoid baseplate 100B or the glenoid baseplate 100A can be about 3 mm in one embodiment. The offset between the longitudinal axis 160 and the center 148 of the glenoid baseplate 100B or the glenoid baseplate 100A can be about 2 mm in one embodiment. The offset between the longitudinal axis 160 and the center 148 of the glenoid baseplate 100B or the glenoid baseplate 100A can be about 1 mm in one embodiment. The offset between the longitudinal axis 160 and the center 148 of the glenoid baseplate 100B or the glenoid baseplate 100A can be about 0.5 mm in one embodiment.

Figure 6A:
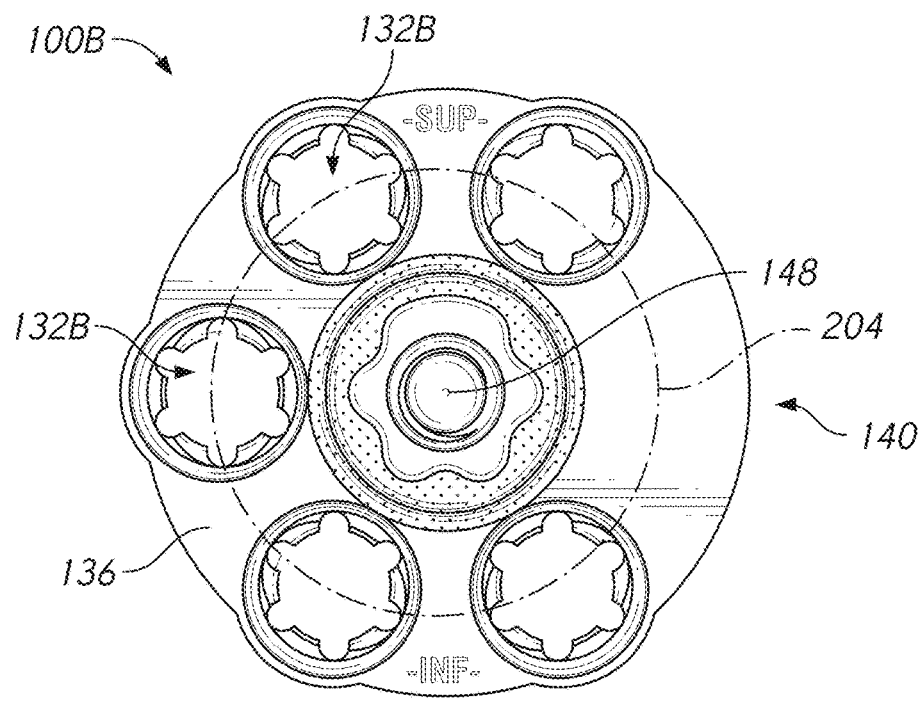
FIG. 6A is a lateral side view of the glenoid baseplate of FIG. 6.

FIG. 6A shows that for some amounts of offset the glenoid baseplate 100D omits one or more anchor apertures 132. As in the glenoid baseplate 100, the aperture circumference 204 provide that anchor apertures 132B are evenly distributed about the second side 124 of the transverse body 104B. The anchor apertures 132B can be spaced apart by even increments. In one or more of the increment positions the transverse body 104B is made solid with no anchor apertures 132B formed therein. The anchor apertures 132B is omitted because the glenoid baseplate 100D has the elongate body 108D disposed at least partially within the area of the anchor apertures 132B that is omitted. Because the elongate body 108D is positioned at this location a bone anchor, such as a bone screw, cannot be placed though this area.

Shoulder Implant Configured From Surgical Planning

The various glenoid baseplates can be better understood with reference to FIGS. 1A-1C, discussed above. The glenoid baseplate 100 can advantageously be formed following step 88 in which imaging information of a scapula 55 is obtained from the imager 80. The imager 80 can be a CT scanner, X-ray, MRI or other similar imaging modality or from a tracer that can be obtain bone shape by direct contact with the bone or with tissue over the bone. The scapula 55 can be characterized in the step 90. This can involve any suitable technique employed by the image processing system 82 for creating a virtual model of the scapula 55, e.g., by segmenting the imaging information to provide a 3D model that can be stored in memory and/or displayed in a graphical user interface. This information can include identifying a center 72 of an inferior portion 70 of the glenoid 58. The center 72 can be identified as a mid-point of a chord of the inferior portion 74 of the glenoid rim 68 of the scapula 55. The chord can be located a distance equal to the radius from the inferior-most point of the inferior portion 74 of the glenoid rim 68. The chord can be located at an inferior-superior position along the glenoid rim 68 between an anterior portion thereof adjacent to the anterior surface 76 of the scapula 55 and a posterior portion thereof adjacent to the posterior surface 78 of the scapula 55. The inferior superior position can be that position where the distance across the glenoid 58 is equal to two times the radius of curvature of the inferior portion 74 of the glenoid rim 68. The glenoid baseplate 100 can be configured such that the transverse body 104 has a round periphery with a radius equal to the radius of curvature of the inferior portion 74 of the glenoid rim 68. The center 148 of the transverse body 104 can be located at the center 72 as determined in the step 90.

The position of the elongate body 108 can be determined in the step 92. The step involves finding an appropriate position for preparing the opening 86 in the surface of the glenoid 58 for receiving the elongate body 108. As noted above, the position may be positioned adjacent to the center 72. The opening 86 may advantageously be formed anterior of the center 72, posterior of the center 72, inferior of the center 72, superior of the center 72, or any combination of anterior, posterior, inferior and superior to the center 72 as needed based on the analysis in step 90. The position of the opening 86 may be selected by finding a location along the line 91 where any combination of the depth, strength, thickness, bone density and bone strength is sufficient to accommodate a minimum length of the elongate body 108. The position of the opening 86 can be one in which the bone will support formation of a blind hole in the scapula 55 extending from the opening 86 to an enclosed end where the entire length of the elongate body 108 can be accommodated in the blind hole. With reference to FIG. 1C the elongate body 108 can have a length that equates to the thickness t2. The positon can be anywhere between the two horizontal lines bounding reference number 86.

The step 94 can include specifying the diameter of the transverse body 104 and the position of elongate body 108. The step 94 can also include specifying the length of the elongate body 108. For patients with larger volume of bone in the scapula 55 the elongate body 108 can be made longer than the minimum length if such additional length is deemed to provide a clinical advantage, e.g., better implants security. The step 94 can also output a baseplate with a threaded hole that extends below the bone surface (as in FIGS. 3-4A) or that is located laterally of the bone when applied to the patient (as in FIGS. 5-6A).

The step 98 can include forming the baseplate through a suitable process such as an additive manufacturing process, e.g., three dimensional printing. Examples of three dimensional printing include direct metal laser sintering (DMLS), fused deposition modeling (FDM), fused filament fabrication (FFF), and electron beam melting (EBM). Any one or a combination of these or other additive manufacturing processes can be used in the step 98. In these processes a three dimensional object is formed by sequentially forming individual layers of the object on top of previously formed individual layers. These processes can closely control the gross dimensions of the object and also can form complex features and shapes such as contours. In certain embodiments, the step 98 can be used to form the first side 120 of any of the glenoid baseplates disclosed herein as complementary surface that can mate with specific anatomy of a specific patient, e.g., with a convex surface that mates with the concave surfaces of the glenoid 58 as show in dash-dot line 99 of FIG. 1.

As discussed further above, the scapula 55 has a thickness between the anterior surface 76 and the posterior surface 78 the scapula can be small and can rapidly and/or unpredictably decrease beneath the glenoid 58. Thickness change beneath the glenoid 58 can be due to many factors including the anterior and posterior surfaces of the scapula being irregular or inconsistent from patient to patient. The foregoing method and apparatus provide for consistently sound anchorage of the projection of the elongate bodies of the glenoid baseplates on the medial side of the baseplate within the wall of the scapula. The applicants of this application have found that for many patient this results in an offset medial post where the post is offset to an anterior zone of the baseplate. These configurations can lead to higher likelihood of clinical success.

Surgical Methods For Baseplates Configured Based on Patient Scapula Anatomy

Figure 7A:
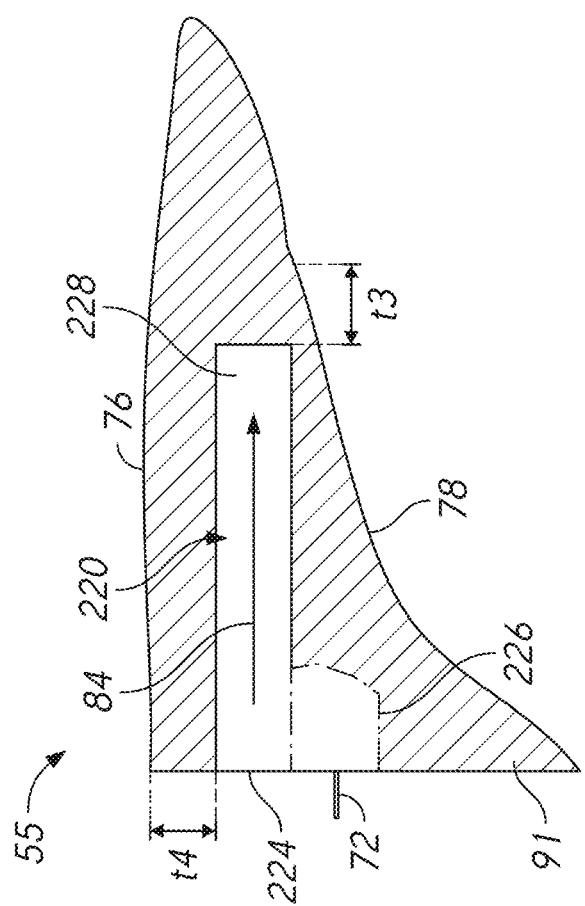
FIGS. 7-7C illustrate various steps of a method of applying a glenoid baseplate to a scapula.
Figure 7:
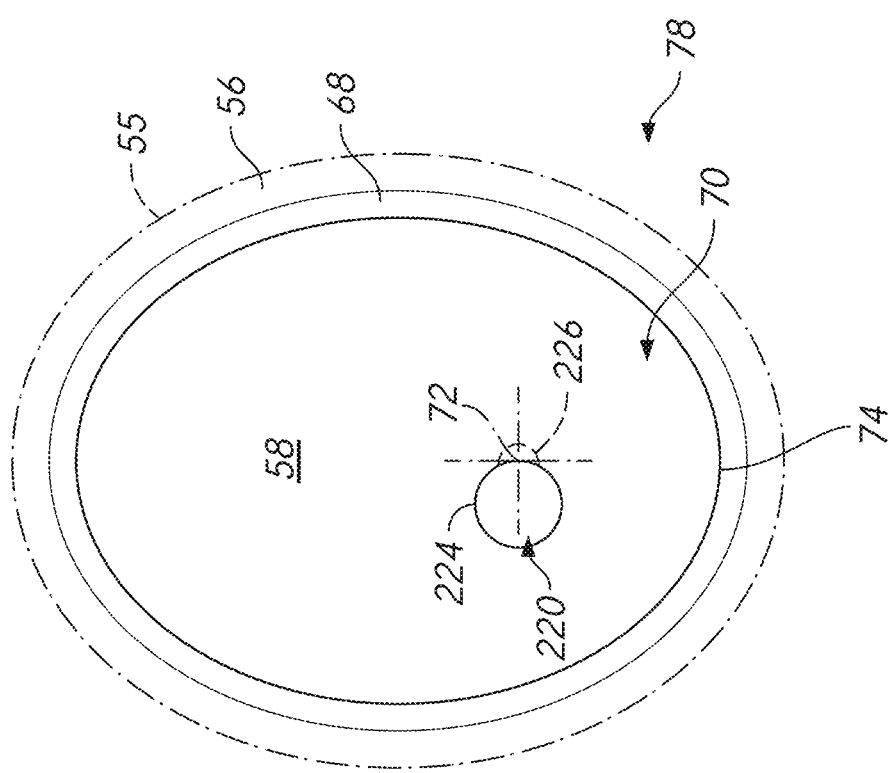
Figure 7B:
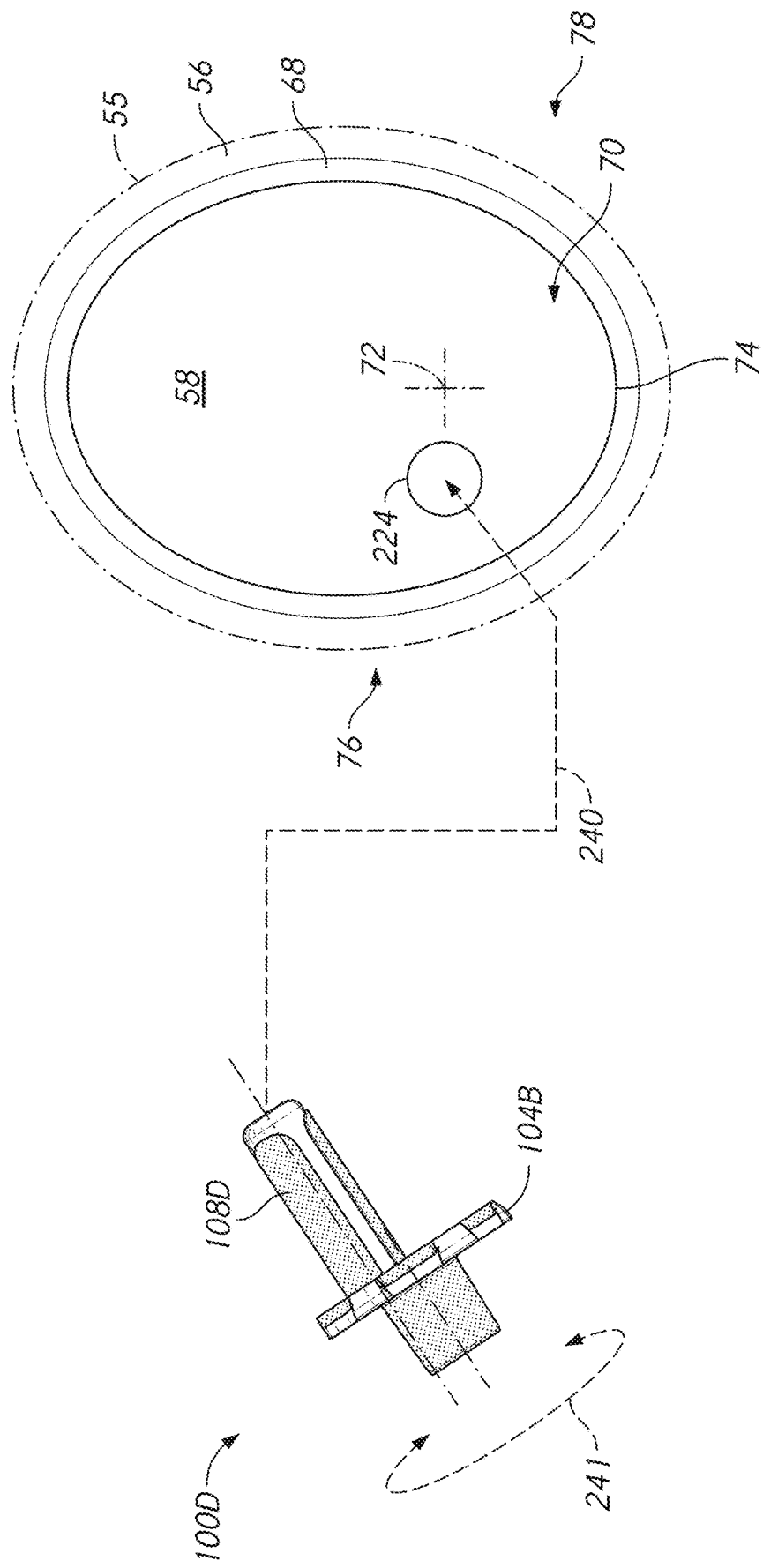
Figure 7C:
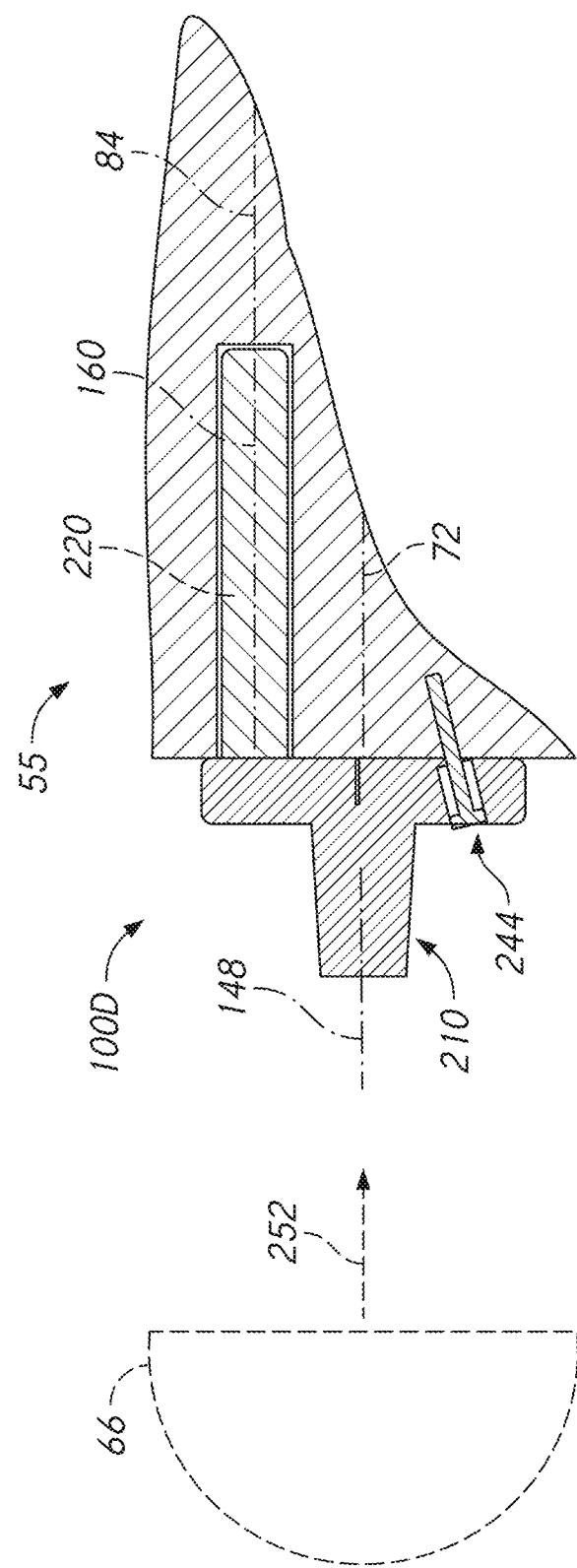

The foregoing disclosure provides for various advantageous surgical methods. FIGS. 7-7C illustrate some of these methods. FIG. 7 shows that a blind hole 220 can be formed in a lateral surface 56 of the scapula 55, e.g., within the surface of the glenoid 58. The blind hole can be formed at location of the opening 86 identified in the method of FIGS. 1A-1C. The blind hole can extend from an opening 224 corresponding to the opening 86 to an enclosed end 228 opposite the opening 224. The enclosed end 228 can be at a depth and at an anterior-posterior position that is spaced apart from the anterior surface 76 and the posterior surface 78 of the scapula 55. The blind hole can extend along an axis that corresponds to the anchor trajectory 84 determined in the method of FIGS. 1A-IC. FIGS. 7 and 7A show that the blind hole 220 is off set from the center 72 of the inferior portion 70 of a glenoid 58.

FIG. 7 shows that for some of the baseplate configurations, the blind hole 220 may be enlarged, e.g., providing an expanded opening 226. The expanded opening 226 can be a portion that extends from the blind hole 220 toward the center 72. For example, the glenoid baseplate 100A includes the fastener body 192A that is aligned with the center 148. The center 148 is to be aligned with the center 72 when the glenoid baseplate 100A is applied. Accordingly the surface of the glenoid 58 may be prepared to enlarge the blind hole 220 include the expanded opening 226 to accommodate the fastener body 192A. The expanded opening 226 is disposed at, over or around the center 72 such that a screw for connecting the articular body 66 to the glenoid baseplate 100A can be centered on the transverse body 104. Forming the expanded opening 226 may be accomplished by a surgical drill, by a small reamer, by a tamp, or in the process of placing a trial implant in the glenoid 58. Or the glenoid baseplate 100A could be advanced into the blind hole 220 and the expanded opening 226 can be formed by compression of the bone as the glenoid baseplate 100A is impacted into the bone.

FIG. 7C shows application of the glenoid baseplate 100D to the glenoid 58. The elongate body 108D can be advanced as indicated by an arrow 240 toward the glenoid 58 such that the elongate body 108D is at the opening 224 to the blind hole 220. The elongate body 108D can be advanced into the blind hole 220 until the elongate body 108D is adjacent to or contacts the enclosed end 228. The elongate body 108D can be advanced into the blind hole 220 until the elongate body transverse body 104B is adjacent to or contacts the glenoid 58. The elongate body 108D can be advanced into the blind hole 220 until a patient matched medial side of the glenoid baseplate 100D as indicated by the dash-dot line 99 in FIG. 1 contacts or nests with the natural or existing concavity of the glenoid 58. The elongate body 108D is located adjacent to or contacts the enclosed end 228.

Prior to advancing the elongate body 108D into the opening 224 the glenoid baseplate 100D can be rotationally oriented as indicated by the arrow 241 relative to the glenoid 58. For example, if there are rotational positioning indicia or features those features can be properly oriented by the surgeon. As noted above, the second side 124 of the transverse body 104B can be marked with "SUP" to indicate the portion of the transverse body 104B that should be oriented superiorly. In some embodiments the tooling interface 212 disposed on the coupling projection 210 of the transverse body 104B can be rotationally asymmetric such that a portion of the instrument that advances or holds the glenoid baseplate 100D can be easily visually confirmed to be properly oriented instead of or in addition to relying marking such as "SUP" for superior, "INF" for inferior, "ANT" for anterior, "POS" for posterior, etc.

FIG. 7C shows that following rotational positioning (if needed) and advancement of the glenoid baseplate 100D into the blind hole 220 the glenoid baseplate 100D can be secured to the scapula 55. One or more bone anchor 244 can be advanced through the transverse body 104B and into the bone. The bone anchor 244 can be directed through the transverse body 104B toward and/or into cortical bone of the scapula 55. In some techniques, the direction of the bone anchor 244 or the length thereof can be planned or selected prior to or during the surgery to assure a particular outcome. For instance the orientation or length can be planned or selected to assure the end of the bone anchor 244 opposite to the end coupled to the transverse body 104B is disposed in the cortical bone but not through the anterior surface 76 or the posterior surface 78 of the scapula 55. The orientation or length can be planned or selected to assure the end of the bone anchor 244 opposite to the end coupled to the transverse body 104B is disposed in the cortical bone and also extends through the anterior surface 76 or the posterior surface 78 of the scapula 55. FIG. 7C shows just one screw placed through the transverse body 104B into the scapula 55. Additional screws can be placed out of the section plane shown, e.g., superior to and/or inferior to the coupling projection 210. As discussed above, the glenoid baseplate 100D is configured such that two anchor apertures 132B are provided in superior and inferior positions and one anchor aperture 132B is provided at a posterior position. An anterior expanse of the transverse body 104B is provided in which the anchor aperture 132B is omitted. FIG. 7C shows that the glenoid baseplate 100D is secured without any bone anchor 244 between the position of the elongate body 108D and the anterior periphery of the transverse body 104B.

FIG. 7C shows that following the securing of the glenoid baseplate 100D to the scapula 55 the articular body 66 can be coupled with the glenoid baseplate 100D. The articular body 66 can be advanced an indicted by arrow 252 toward the coupling projection 210. The coupling projection 210 can be received in a corresponding tapered recess formed in the medial side of the articular body 66. The tapered recess and the coupling projection 210 can be configured to form a Morse taper connection. The Morse taper connection be sufficient to secure the articular body 66 to the glenoid baseplate 100D. In some embodiments, additional securement can be provided by a screw advanced through the articular body 66 into the threaded hole 180B of the coupling projection 210. The screw can engage threads in the threaded hole 180B as it is advanced from the open end 184B toward the enclosed end 188B. In some embodiments, a screw can provide the sole connection between the articular body 66 and the glenoid baseplate 100D by being advanced into the threaded hole 180B of the coupling projection 210, engaging threads in the threaded hole 180B as it is advanced from the open end 184B toward the enclosed end 188B.

Terminology

As used herein, the relative terms "lateral" and "medial" shall be defined relative to the anatomy. Thus, medial refers to the direction toward the midline and lateral refers to the direction away from the midline.

Although certain embodiments and examples have been described herein, it will be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±1%, ±5%, ±10%, ±15%, etc.). For example, "about 0.01 inches" includes "0.01 inches." Phrases preceded by a term such as "substantially" include the recited phrase and should be interpreted based on the circumstances (e.g., as much as reasonably possible under the circumstances). For example, "substantially linear" includes "linear."

What is claimed is:

1. A glenoid baseplate, comprising:
   a transverse body comprising a first side configured to engage scapula bone of a patient, a second side configured to face away from the first side, a plurality of anchor apertures formed between the first side and the second side, and a circular periphery extending between the first side and the second side, the circular periphery having an anterior portion configured to be oriented toward an anterior side of a scapula, a posterior portion configured to be oriented toward a posterior side of the scapula, and a center;
   an elongate body disposed along a longitudinal axis between a first end and a second end, the second end being coupled with the first side of the transverse body and the first end being disposed away from the second end;
   a fastener body having a first end and a second end, wherein the fastener body is configured as a transverse extension of the elongate body, the second end of the fastener body being coupled with the first side of the transverse body and the fastener body extends away from the first side of the transverse body along the elongate body and toward the first end of the elongate body; and
   a threaded hole provided within the transverse body and extending into the fastener body for facilitating a connection of an articular body to the glenoid baseplate;
   wherein the longitudinal axis of the elongate body is offset from the center of the circular periphery toward the anterior portion thereof.

2. The glenoid baseplate of claim 1, wherein the threaded hole is disposed at the center of the circular periphery.

3. The glenoid baseplate of claim 1, wherein the threaded hole is a blind hole with an open end on the second side of the transverse body and an enclosed end opposite the open end.

4. The glenoid baseplate of claim 3, wherein the enclosed end of the blind hole is disposed between the first end of the transverse body and the first end of the elongate body.

5. The glenoid baseplate of claim 1, wherein the circular periphery of the transverse body comprises a tapered profile configured to mate with a tapered recess of an articular body.

6. The glenoid baseplate of claim 1, wherein the anchor apertures are evenly distributed about the transverse body.

7. The glenoid baseplate of claim 1, wherein the anchor apertures are evenly distributed about an aperture circumference of the transverse body, an anterior portion of the aperture circumference opposite the elongate body being formed without an aperture.

8. A glenoid baseplate, comprising:
   a transverse plate having a medial side configured to engage scapula bone of a patient, a lateral side configured to face away from the medial side, a plurality of bone screw holes formed between the medial side and the lateral side, and a circular periphery extending between the medial side and the lateral side, the circular periphery having an anterior portion configured to be oriented toward an anterior side of a scapula, a posterior portion configured to be oriented toward a posterior side of the scapula, and a center;

an anchor peg disposed along a longitudinal axis between a lateral end that is coupled with the medial side of the transverse plate and a medial end that is disposed away from the lateral end;

a fastener body having a first end and a second end, wherein the fastener body is configured as a transverse extension of the anchor peg, the second end of the fastener body being coupled with the medial side of the transverse plate and the fastener body extends away from the first side of the transverse plate along the anchor peg and toward the lateral end of the anchor peg; and a threaded hole provided within the transverse plate and extending into the fastener body for facilitating a connection of an articular body to the glenoid baseplate;

wherein the longitudinal axis of the anchor peg is offset from the center of the circular periphery toward the anterior portion thereof.

9. The glenoid baseplate of claim 8, wherein the threaded hole is a blind hole with an open end that opens up on the lateral side of the transverse plate.

10. A method, comprising:

providing a glenoid anchor having a transverse member having a medial side, a lateral side, an anterior periphery, a posterior periphery, an anchor peg extending from the medial side and disposed along a longitudinal axis between a lateral end and a medial end, the lateral end of the anchor peg being coupled with the medial side of the transverse member and the medial end of the anchor peg being disposed away from the lateral side of the transverse member, the anchor peg being located closer to the anterior periphery than to the posterior periphery, and a fastener body having a first end and a second end, wherein the fastener body is configured as a transverse extension of the anchor peg, the second end of the fastener body being coupled with the medial side of the transverse member and the fastener body extends away from the medial side of the transverse member and toward the medial end of the anchor peg; and a threaded hole provided within the transverse member and extending into the fastener body, wherein the threaded hole is a blind hole with an open end that opens up on the lateral side of the transverse member;

forming a blind hole in a lateral portion of the scapula along a trajectory that is off set from a center of an inferior portion of a glenoid, the blind hole having an opening at the glenoid and an enclosed end opposite the opening, the enclosed end being spaced apart from an anterior surface of the scapula, and the enclosed end being spaced apart from a posterior surface of the scapula; and advancing the anchor peg of the glenoid anchor into the blind hole such that the anchor peg is enclosed within the scapula along the blind hole between the opening and the enclosed end.

11. The method of claim 10, further comprising orienting the anchor peg of the glenoid anchor toward an anterior portion of a rim of the glenoid prior to advancing the anchor peg of the glenoid anchor into the blind hole.

12. A method, comprising:

receiving image data responsive to a scan of a scapula of a patient;

identifying from the image data an anchor trajectory extending medially from a lateral surface of the scapula, the anchor trajectory being at a selected position relative to an anterior surface of the scapula and a posterior surface of the scapula;

forming a glenoid anchor having a transverse member having a medial side, a lateral side, an anterior periphery, a posterior periphery, a projection extending from the medial side and disposed along a longitudinal axis between a first end and a second end, the second end being coupled with the medial side of the transverse member and the first end being disposed away from the second end, the projection being located closer to the anterior periphery than to the posterior periphery, and a fastener body having a first end and a second end, wherein the fastener body is configured as a transverse extension of the projection, the second end of the fastener body being coupled with the medial side of the transverse member and the fastener body extends away from the medial side of the transverse member along the projection and toward the first end of the projection; and a threaded hole provided within the transverse member and extending into the fastener body, wherein the threaded hole is a blind hole with an open end that opens up on the lateral side of the transverse member;

wherein the projection is disposed within the periphery at a location aligned with the identified anchor trajectory when the periphery is aligned with the curvature of the inferior portion of the glenoid rim.

13. The method of claim 12, wherein the anchor trajectory is spaced apart from the anterior surface of the scapula.

14. The method of claim 12, wherein the anchor trajectory is spaced apart from the posterior surface of the scapula.

15. The method of claim 14, wherein the anchor trajectory is spaced apart from the anterior surface of the scapula.

16. The method of claim 12, wherein the glenoid anchor is formed such that the projection extending from the medial side is configured to extend through opposing cortical bone of the scapula.

* * * * *